United States Patent
Woller et al.

(10) Patent No.: US 8,637,529 B2
(45) Date of Patent: Jan. 28, 2014

(54) PYRAZOLO[3,4-D]PYRIMIDINE COMPOUNDS

(75) Inventors: Kevin R. Woller, Anitoch, IL (US); Michael L. Curtin, Pleasant Prairie, WI (US); Kristine E. Frank, Worcester, MA (US); Nathan S. Josephsohn, Marlborough, MA (US); Biqin C. Li, Northborough, MA (US); Neil Wishart, Jefferson, MA (US)

(73) Assignee: AbbVie Inc., North Chicago, IL (US)

( * ) Notice: Subject to any disclaimer, the term of this patent is extended or adjusted under 35 U.S.C. 154(b) by 45 days.

(21) Appl. No.: 13/157,777

(22) Filed: Jun. 10, 2011

(65) Prior Publication Data

US 2012/0015963 A1    Jan. 19, 2012

Related U.S. Application Data

(60) Provisional application No. 61/353,862, filed on Jun. 11, 2010.

(51) Int. Cl.
*A01N 43/90* (2006.01)
*A61K 31/519* (2006.01)
*C07D 487/00* (2006.01)

(52) U.S. Cl.
USPC ........................................ 514/262.1; 544/262

(58) Field of Classification Search
None
See application file for complete search history.

(56) References Cited

U.S. PATENT DOCUMENTS

| | | |
|---|---|---|
| 7,772,231 B2 | 8/2010 | Sheppard et al. |
| 2004/0023992 A1 | 2/2004 | Das et al. |
| 2008/0070914 A1 | 3/2008 | Freyne et al. |
| 2009/0312338 A1 | 12/2009 | Wishart et al. |
| 2011/0190489 A1 | 8/2011 | Wishart et al. |

FOREIGN PATENT DOCUMENTS

| | | |
|---|---|---|
| GB | 716327 | * 10/1954 |
| WO | 2004065378 A1 | 8/2004 |
| WO | 2006074984 A1 | 7/2006 |
| WO | 2006074985 A1 | 7/2006 |
| WO | 2008/094602 A2 | 8/2008 |
| WO | 2008094602 A2 | 8/2008 |

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
Hauser, et. al., Journal of Organic Chemistry (1961), 26, 451-5.*
Mikhaleva, et al., Khimiya Geterotsiklicheskikh Soedinenii (1972), (12), 1696-9.
U.S. Appl. No. 12/958,115, Abbott Laboratories.

* cited by examiner

*Primary Examiner* — Jeffrey Murray
(74) *Attorney, Agent, or Firm* — Gayle O'Brien

(57) ABSTRACT

The present disclosure is directed to novel compounds of Formula (I)

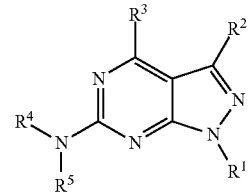

Formula (I)

pharmaceutically acceptable salts, pro-drugs, biologically active metabolites, stereoisomers and isomers thereof wherein the variables are as defined herein. The compounds of Formula (I) are useful as kinase inhibitors and as such would be useful in treating certain conditions and diseases, especially inflammatory conditions and diseases and proliferative disorders and conditions, for example, rheumatoid arthritis, systemic lupus erythematosus, multiple sclerosis, Crohn's disease, psoriasis and asthma.

17 Claims, No Drawings

PYRAZOLO[3,4-D]PYRIMIDINE COMPOUNDS

CROSS REFERENCE TO RELATED APPLICATION

This application claims priority to U.S. Provisional Application Ser. No. 61/353,862 filed on Jun. 11, 2010, the contents of which are incorporated herein.

BACKGROUND OF THE INVENTION

The invention provides a novel class of compounds, pharmaceutical compositions comprising such compounds and methods of using such compounds to treat or prevent diseases or disorders associated with abnormal or deregulated kinase activity, particularly diseases or disorders that involve abnormal activation of the Jak1, Jak2, Jak3, Tyk2, KDR, Flt-3, CDK2, CDK4, TANK, Trk, FAK, Abl, Bcr-Abl, cMet, b-RAF, FGFR3, c-kit, PDGF-R, PKC kinases or Aurora kinases.

The protein kinases represent a large family of proteins that play a central role in the regulation of a wide variety of cellular processes and maintenance of cellular function. A partial, non-limiting, list of these kinases include: non-receptor tyrosine kinases such as the Janus kinase family (Jak1, Jak2, Jak3 and Tyk2); the fusion kinases, such as BCR-Abl, focal adhesion kinase (FAK), Fes, Lck and Syk; receptor tyrosine kinases such as platelet-derived growth factor receptor kinase (PDGF-R), the receptor kinase for stem cell factor, c-kit, the nerve growth factor receptor, c-Met, and the fibroblast growth factor receptor, FGFR3; and serine/threonine kinases such as b-RAF, mitogen-activated protein kinases (e.g., MKK6) and SAPK2β. Aberrant kinase activity has been observed in many disease states including benign and malignant proliferative disorders as well as diseases resulting from inappropriate activation of the immune and nervous systems. The novel compounds of this invention inhibit the activity of one or more protein kinases and are, therefore, expected to be useful in the treatment of kinase-mediated diseases.

SUMMARY OF THE INVENTION

In a first embodiment the invention provides a compound of Formula (I)

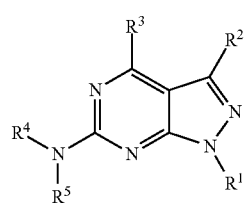

Formula (I)

and pharmaceutically acceptable salts, pro-drugs, biologically active metabolites, stereoisomers and isomers thereof wherein $R^1$ is —W—X—Y wherein W is directly attached to the nitrogen of the pyrazolyl ring;

W is a bond, phenylene, optionally substituted ($C_1$-$C_6$) alkylene, optionally substituted bridged ($C_2$-$C_{10}$)heterocyclylene, ($C_3$-$C_6$)cycloalkylene, optionally substituted heterocyclylene or optionally substituted heteroarylene;

X is a bond, phenylene, optionally substituted ($C_3$-$C_6$) cycloalkylene, optionally substituted piperidine or optionally substituted heteroarylene;

Y is H, deuterium, oxo, —C(O)$R^a$, —S(O)$_2$N($R^a$)$_2$, —N($R^a$)S(O)$_2$—, —O$R^a$, —N($R^a$)S(O)$_2$$R^a$, —C(O) N($R^a$)$_2$, —N($R^a$)C(O)$R^a$, —N($R^a$)$_2$, —S(O)$_2$$R^a$, —CH$_3$, —CH$_2$NH$_2$, — optionally substituted ($C_1$-$C_6$)alkylene, —N($R^a$)C(O)O—$R^a$, or optionally substituted ($C_1$-$C_6$)alkyl, provided that when W and X are both bonds then Y is not oxo, —N($R^a$)S(O)$_2$$R^a$, —N($R^a$)C(O)$R^a$ or —N($R^a$)$_2$; or Y is A-D wherein A is connected to X wherein A is a bond, C(O), C(O)$R^b$, $R^b$C(O), S(O)$_2$, optionally substituted ($C_1$-$C_6$)alkylene, N($R^a$)S(O)$_2$$R^b$, $R^b$S (O)$_2$N($R^a$), N($R^a$)C(O), C(O)N($R^a$), N($R^a$)S(O)$_2$, S(O)$_2$N($R^a$), 0, O$R^b$, $R^b$O, N($R^a$)$R^b$, $R^b$N($R^a$), $R^b$N($R^a$)C(O), C(O)N($R^a$)$R^b$, $R^b$N($R^a$)S(O)$_2$, S(O)$_2$N($R^a$)$R^b$, N($R^a$)C(O)$R^b$, $R^b$C(O)N($R^a$), $R^b$N ($R^a$), S(O)$_2$$R^b$, $R^b$S(O)$_2$, and N($R^a$); and D is —CN, —C(O)N($R^a$)$_2$ or —N($R^a$)$_2$; or D is —O-optionally substituted ($C_1$-$C_6$)alkyl, optionally substituted aryl, optionally substituted ($C_3$-$C_{10}$)cycloalkyl, optionally substituted heterocyclyl or optionally substituted heteroaryl;

wherein D may be optionally substituted by one or more —CN, halogen, —OH, —C(O)$R^a$, —$R^a$, —C(O)N($R^a$)$_2$, —O—$R^a$, —N($R^a$)S(O)$_2$$R^a$, —S—$R^a$, —S(O)—$R^a$, —S(O)$_2$—$R^a$ or —S(O)$_2$N($R^a$)$_2$;

provided that $R^1$ is not biphenyl, optionally substituted indanyl, optionally substituted indenyl, optionally substituted indolyl or optionally substituted tetrahydrofuranyl; or $R^1$ is

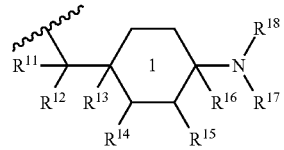

wherein $R^{11}$, $R^{12}$, $R^{13}$, $R^{14}$, $R^{15}$ and $R^{16}$ are independently H, CN, OH, optionally substituted ($C_1$-$C_6$) alkyl, —O-optionally substituted ($C_1$-$C_6$)alkyl or optionally substituted ($C_3$-$C_{10}$)cycloalkyl; or $R^2$ is H, deuterium, CN, C≡CH, optionally substituted ($C_1$-$C_8$)alkyl, optionally substituted ($C_3$-$C_{10}$)cycloalkyl, —C(O)-optionally substituted ($C_1$-$C_4$)alkyl or —C(O)N($R^a$)$_2$;

$R^3$ is H, deuterium, or optionally substituted ($C_1$-$C_4$)alkyl;

$R^4$ is H or optionally substituted ($C_1$-$C_4$)alkyl;

$R^5$ is -G-J wherein G is connected to the nitrogen atom and wherein

G is a bond, optionally substituted ($C_3$-$C_{10}$)cycloalkylene, pyrazole or phenylene;

wherein the phenylene is optionally substituted with CH$_3$; and

J is H, optionally substituted ($C_1$-$C_3$)alkyl, —O$R^a$, —C(O)$R^a$, —C(O)N($R^a$)$_2$, —S$R^a$—, —S(O)$_2$—$R^b$, —S(O)$_2$—N($R^a$)$_2$, —S(O)$_2$—NH—C(O)—$R^a$, optionally substituted heteroaryl, optionally substituted morpholinyl, optionally substituted thiomorpholinyl or optionally substituted piperazinyl;

wherein the piperazinyl is optionally substituted with CH$_3$ and provided that J is not triazolyl; or $R^4$ and $R^5$ fuse to form a $(C_2-C_4)$heterocyclic ring which can be optionally substituted;

$R^a$ is independently H, deuterium, optionally substituted $(C_1-C_6)$alkyl, optionally substituted $(C_3-C_{10})$cycloalkyl, optionally substituted aryl, or optionally substituted heteroaryl; and $R^b$ is independently optionally substituted $(C_1-C_6)$alkyl, optionally substituted $(C_3-C_{10})$cycloalkyl, optionally substituted aryl, optionally substituted heteroaryl or optionally substituted heterocyclyl;

and provided that the compound is not 1-isopropyl-4-methyl-N-(5-(piperazin-1-yl)pyridin-2-yl)-1H-pyrazolo[3,4-d]pyrimidin-6-amine;

tert-butyl 4-(6-(4-(4-methylpiperazin-1-yl)phenylamino)-1H-pyrazolo[3,4-d]pyrimidine-1-yl)cyclohexyl carbamate;

1-cyclopentyl-N-(4-(4-methylpiperazin-1-yl)phenyl)-1H-pyrazolo[3,4-d]pyrimdin-6-amine;

1-cyclohexyl-N-(4-(4-methylpiperazin-1-yl)phenyl)-1H-pyrazolo[3,4-d]pyrimidine-6-amine;

1-cyclohexyl-N-(4-(piperazin-1-yl)phenyl)-1H-pyrazolo[3,4-d]pyrimidin-6-amine; or tert-butyl 4-((1-cyclohexyl-1H-pyrazolo[3,4-d]pyrimidin-6-yl)amino)benzoate.

In a second embodiment the invention provides a compound according to the first embodiment wherein $R^2$ is H.

In a third embodiment the invention provides a compound according to any of the foregoing embodiments wherein $R^3$ is H.

In a fourth embodiment the invention provides a compound according to any of the foregoing embodiments wherein $R^4$ is H.

In a fifth embodiment the invention provides a compound according to any of the foregoing embodiments wherein $R^1$ is —W—X—Y wherein W is directly attached to the nitrogen of the pyrazolyl ring;

W is a bond, optionally substituted $(C_1-C_6)$alkylene, phenylene, optionally substituted $(C_3-C_6)$cycloalkylene, optionally substituted heterocyclylene or optionally substituted heteroarylene;

X is a bond, phenylene, optionally substituted $(C_3-C_6)$cycloalkylene, optionally substituted piperidine or optionally substituted pyridine;

Y is H, oxo, —C(O)$R^a$, —S(O)$_2$N($R^a$)$_2$, —N($R^a$)S(O)$_2$, —O$R^a$, —N($R^a$)S(O)$_2$$R^a$, —C(O)N($R^a$)$_2$, —N($R^a$)C(O)$R^a$, —N($R^a$)$_2$, —S(O)$_2$$R^a$, —CH$_3$ or —CH$_2$NH$_2$, provided that when W and X are both bonds that Y is not oxo, —N($R^a$)S(O)$_2$, —N($R^a$)S(O)$_2$$R^a$, —N($R^a$)C(O)$R^a$ or —N($R^a$)$_2$; or Y is A-D wherein A is connected to X wherein A is a bond, C(O), C(O)$R^b$, $R^b$C(O), S(O)$_2$, optionally substituted $(C_1-C_6)$alkylene, N($R^a$)S(O)$_2$$R^b$, N($R^a$)C(O), C(O)N($R^a$), N($R^a$)S(O)$_2$, S(O)$_2$N($R^a$), O, O$R^b$, $R^b$O, N($R^a$)$R^b$, $R^b$N($R^a$), $R^b$N($R^a$)C(O), C(O)N($R^a$)$R^b$, $R^b$N($R^a$)S(O)$_2$, N($R^a$)C(O)$R^b$, $R^b$C(O)N($R^a$), $R^b$N($R^a$), $R^b$N($R^a$)S(O)$^2$, S(O)$_2$$R^b$, $R^b$S(O)$_2$, or N($R^a$); and D is —CN, —C(O)N($R^a$)$_2$ or —N($R^a$)$_2$; or D is —O-optionally substituted $(C_1-C_6)$alkyl, optionally substituted aryl, optionally substituted $(C_3-C_{10})$cycloalkyl, optionally substituted heterocyclyl or optionally substituted heteroaryl;

wherein D may be optionally substituted by one or more —CN, halogen, —OH, —C(O)— $(C_1-C_6)$alkyl, —C(O)N($R^a$)$_2$, —O—$(C_1-C_6)$alkyl, —N($R^a$)S(O)$_2$$R^a$, —S—$(C_1-C_6)$alkyl, —S(O)—$(C_1-C_6)$alkyl, —S(O)$_2$—$(C_1-C_6)$alkyl or —S(O)$_2$N($R^a$)$_2$.

In a sixth embodiment the invention provides a compound according to any of the foregoing embodiments wherein Y is A-D wherein A is connected to X wherein A is a bond, C(O), C(O)$R^b$, $R^b$C(O), S(O)$_2$, optionally substituted $(C_1-C_6)$alkylene, N($R^a$)S(O)$_2$$R^b$, N($R^a$)C(O), C(O)N($R^a$), N($R^a$)S(O)$_2$, S(O)$_2$N($R^a$), O, O$R^b$, $R^b$O, N($R^a$)$R^b$, $R^b$N($R^a$), $R^b$N($R^a$)C(O), C(O)N($R^a$)$R^b$, $R^b$N($R^a$)S(O)$_2$, N($R^a$)C(O)$R^b$, $R^b$C(O)N($R^a$), $R^b$N($R^a$), $R^b$N($R^a$)S(O)$_2$, S(O)$_2$$R^b$, $R^b$S(O)$_2$, and N($R^a$); and D is —CN, —C(O)N($R^a$)$_2$ or —N($R^a$)$_2$; or D is, —O-optionally substituted $(C_1-C_6)$alkyl, optionally substituted aryl, optionally substituted $(C_3-C_{10})$cycloalkyl, optionally substituted heterocyclyl or optionally substituted heteroaryl;

wherein D may be optionally substituted by one or more —CN, halogen, —OH, —C(O)—$(C_1-C_6)$alkyl, —C(O)N($R^a$)$_2$, —O—$(C_1-C_6)$alkyl, —N($R^a$)S(O)$_2$$R^a$, —S—$(C_1-C_6)$alkyl, —S(O)—$(C_1-C_6)$alkyl, —S(O)$_2$—$(C_1-C_6)$alkyl or —S(O)$_2$N($R^a$)$_2$.

In a seventh embodiment the invention provides a compound according to any of the foregoing embodiments wherein Y is H, —S(O)$_2$N($R^a$)$_2$, —N($R^a$)S(O)$_2$, —O$R^a$, —C(O)N($R^a$)$_2$, —N($R^a$)C(O)$R^a$, —N($R^a$)$_2$, —CH$_3$ or —CH$_2$NH$_2$; or Y is A-D wherein A is a bond, C(O), S(O)$_2$, optionally substituted $(C_1-C_6)$alkylene, N($R^a$)S(O)$_2$$R^b$, N($R^a$)C(O), C(O)N($R^a$), N($R^a$)S(O)$_2$, S(O)$_2$N($R^a$), O, O$R^b$, $R^b$N($R^a$), $R^b$N($R^a$)C(O), C(O)N($R^a$)$R^b$, $R^b$N($R^a$)S(O)$_2$, N($R^a$)C(O)$R^b$, or $R^b$C(O)N($R^a$), and D is —CN, —C(O)N($R^a$)$_2$, —N($R^a$)$_2$, or —O-optionally substituted $(C_1-C_6)$alkyl;

or

D is optionally substituted aryl, optionally substituted $(C_3-C_{10})$cycloalkyl, optionally substituted heterocyclyl or optionally substituted heteroaryl;

wherein D may be optionally substituted by one or more —CN, halogen, —OH, —C(O)—$(C_1-C_6)$alkyl, —C(O)N($R^a$)$_2$, —O—$(C_1-C_6)$alkyl, —N($R^a$)S(O)$_2$$R^a$, —S—$(C_1-C_6)$alkyl, —S(O)—$(C_1-C_6)$alkyl, —S(O)$_2$—$(C_1-C_6)$alkyl or —S(O)$_2$N($R^a$)$_2$.

In an eighth embodiment the invention provides a compound according to any of the foregoing embodiments wherein W is a bond or optionally substituted $(C_1-C_6)$alkylene;

X is a bond, optionally substituted phenylene, optionally substituted $(C_3-C_6)$cycloalkylene, or optionally substituted piperidine;

Y is H, —S(O)$_2$N($R^a$)$_2$, —N($R^a$)S(O)$_2$, —O$R^a$, —C(O)N($R^a$)$_2$, —N($R^a$)C(O)$R^a$, —N($R^a$)$_2$, or optionally substituted $(C_1-C_6)$alkyl; or Y is A-D wherein A is connected to X wherein A is a bond, C(O), N($R^a$)C(O), or $R^b$N($R^a$)C(O); and D is —CN, C(O)N($R^a$)$_2$, —N($R^a$)$_2$, or —O-optionally substituted $(C_1-C_6)$alkyl.

In a ninth embodiment the invention provides a compound according to any of the foregoing embodiments wherein $R^4$ is H or optionally substituted $(C_1-C_4)$alkyl;

$R^5$ is -G-J wherein G is connected to the nitrogen atom and wherein

G is a bond, optionally substituted $(C_3-C_{10})$cycloalkylene, pyrazole or phenylene;

wherein the phenylene is optionally substituted with CH$_3$; and

J is H, optionally substituted (C$_1$-C$_3$)alkyl, —OH, —OCH$_3$, —C(O)R$^a$, —C(O)N(R$^a$)$_2$, —SR$^a$—, —S(O)$_2$—CH$_3$, —S(O)$_2$-optionally substituted (C$_1$-C$_3$)alkyl, —S(O)$_2$—N(R$^a$)$_2$, —optionally substituted phenyl, —S(O)$_2$—N(R$^a$)—C(O)—R$^a$, —S(O)$_2$-morpholine, optionally substituted imidazolyl, optionally substituted morpholinyl, optionally substituted thiomorpholinyl or optionally substituted piperazinyl;

wherein R$^a$ is independently H or optionally substituted (C$_1$-C$_6$)alkyl.

In a tenth embodiment the invention provides a compound according to the fourth embodiment wherein R$^1$ is

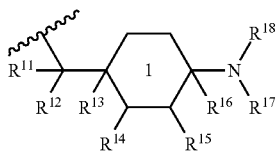

wherein R$^{11}$, R$^{12}$, R$^{13}$, R$^{14}$, R$^{15}$ and R$^{16}$ are independently H, —CN, —OH, optionally substituted (C$_1$-C$_6$)alkyl, —O-optionally substituted (C$_1$-C$_6$)alkyl or optionally substituted (C$_3$-C$_{10}$)cycloalkyl; or R$^{13}$ and R$^{16}$ together form an optionally substituted carbocyclic ring or an optionally substituted heterocyclic ring; or R$^{11}$ and R$^{12}$ together form an optionally substituted carbocyclic ring, an optionally substituted heterocyclic ring or an optionally substituted spirocyclic ring; or R$^{11}$ and R$^{13}$ together form an optionally substituted carbocyclic ring or optionally substituted heterocyclic ring; or R$^{16}$ and R$^{17}$ together form an optionally substituted carbocyclic ring or optionally substituted heterocyclic ring; or R$^{15}$ and R$^{17}$ together with the nitrogen to which R$^{17}$ is attached form heterocyclic ring fused to Ring 1; or R$^{17}$ and R$^{18}$ are independently H, —S(O)$_2$-optionally substituted (C$_3$-C$_{10}$)cycloalkyl, —S(O)$_2$-optionally substituted aryl, —S(O)$_2$-optionally substituted (C$_1$-C$_6$)alkyl, —S(O)$_2$, —S(O)$_2$-optionally substituted heterocyclyl, —S(O)$_2$-optionally substituted heteroaryl, —C(O)-optionally substituted (C$_3$-C$_{10}$)cycloalkyl, —C(O)-optionally substituted aryl, —C(O)-optionally substituted (C$_1$-C$_6$)alkyl, —C(O)-optionally substituted heterocyclyl- or —C(O)-optionally substituted heteroaryl; or R$^{17}$ and R$^{18}$ form a heterocyclic ring together with the nitrogen to which they are attached.

In an eleventh embodiment the invention provides a compound according to any of the foregoing embodiments wherein R$^{11}$, R$^{12}$, R$^{13}$, R$^{14}$, R$^{15}$ and R$^{16}$ are independently H, CN, OH, optionally substituted (C$_1$-C$_6$)alkyl, —O-optionally substituted (C$_1$-C$_6$)alkyl or optionally substituted (C$_3$-C$_{10}$) cycloalkyl.

In a twelfth embodiment the invention provides a compound according to any of the foregoing embodiments wherein R$^{13}$ and R$^{16}$ together form an optionally substituted carbocyclic ring or an optionally substituted heterocyclic ring.

In a thirteenth embodiment the invention provides a compound according to any of the first through tenth embodiments wherein R$^{11}$ and R$^{12}$ together form an optionally substituted carbocyclic ring, an optionally substituted heterocyclic ring or an optionally substituted spirocyclic ring.

In a fourteenth embodiment the invention provides a compound according to any of the first through tenth embodiments wherein R$^{16}$ and R$^{17}$ together form an optionally substituted carbocyclic ring or optionally substituted heterocyclic ring.

In a fifteenth embodiment the invention provides a compound according to the first through tenth embodiments wherein R$^{15}$ and R$^{17}$ together with the nitrogen to which R$^{17}$ is attached form heterocyclic ring fused to Ring 1.

In a sixteenth embodiment the invention provides a compound according to the first through tenth embodiments wherein R$^{17}$ and R$^{18}$ are independently H, —S(O)$_2$-optionally substituted (C$_3$-C$_{10}$)cycloalkyl, —S(O)$_2$-optionally substituted aryl, —S(O)$_2$-optionally substituted (C$_1$-C$_6$)alkyl, —S(O)$_2$, —S(O)$_2$-optionally substituted heterocyclyl, —S(O)$_2$-optionally substituted heteroaryl, —C(O)-optionally substituted (C$_3$-C$_{10}$)cycloalkyl, —C(O)-optionally substituted aryl, —C(O)-optionally substituted (C$_1$-C$_6$)alkyl, —C(O)-optionally substituted heterocyclyl- or —C(O)-optionally substituted heteroaryl; or R$^{17}$ and R$^{18}$ form a heterocyclic ring together with the nitrogen to which they are attached.

In a seventeenth embodiment the invention provides a compound according to the first through tenth embodiments wherein R$^5$ is -G-J wherein G is connected to the nitrogen atom and wherein G is a bond, optionally substituted (C$_3$-C$_{10}$)cycloalkylene, optionally substituted pyrazole or phenylene optionally substituted with CH$_3$; and J is H, optionally substituted (C$_1$-C$_6$)alkyl, —OR$^a$, —C(O)R$^a$, —SR$^a$—, —S(O)$_2$—R$^a$, —S(O)$_2$—N(R$^a$)$_2$, —S(O)$_2$—NH—C(O)—R$^a$, optionally substituted heteroaryl, or optionally substituted heterocyclyl;

wherein R$^a$ is independently H, deuterium, optionally substituted (C$_1$-C$_6$)alkyl, optionally substituted (C$_3$-C$_{10}$) cycloalkyl, or optionally substituted heteroaryl; and R$^b$ is independently optionally substituted (C$_1$-C$_6$)alkyl, optionally substituted (C$_3$-C$_{10}$)cycloalkyl, optionally substituted aryl, optionally substituted heteroaryl or optionally substituted heterocyclyl.

In an eighteenth embodiment the invention provides a compound according to the seventeenth embodiment wherein R$^4$ and R$^5$ together form an optionally substituted heterocyclic ring.

In a nineteenth embodiment the invention provides a compound according to the first embodiment wherein the compound is tert-Butyl-cis-4-((6-(4-methyl-3-sulfamoylphenylamino)-1H-pyrazolo[3,4-d]pyrimidin-1-yl)methyl)cyclohexylcarbamate;

tert-Butyl ((1R,4R)-4-((6-(4-(4-methylpiperazin-1-yl)phenylamino)-1H-pyrazolo[3,4-d]pyrimidin-1-yl)methyl)cyclohexyl)methylcarbamate;

3-(1-(3-(N,N-dimethylsulfamoyl)phenyl)-1H-pyrazolo[3,4-d]pyrimidin-6-ylamino)-N,N-dimethylbenzenesulfonamide;

tert-butyl(1R,4R)-4-((6-(3-sulfamoylphenylamino)-1H-pyrazolo[3,4-d]pyrimidin-1-yl)methyl)cyclohexyl)methylcarbamate;

tert-butyl(1R,4R)-4-((6-(4-(4-methylpiperazin-1-yl)phenylamino)-1H-pyrazolo[3,4-d]pyrimidin-1-yl)methyl)cyclohexylcarbamate;

tert-butyl 4-(6-(4-methyl-3-sulfamoylphenylamino)-1H-pyrazolo[3,4-d]pyrimidin-1-yl)piperidine-1-carboxylate;

tert-butyl 4-(6-(4-(4-methylpiperazin-1-yl)phenylamino)-1H-pyrazolo[3,4-d]pyrimidin-1-yl)piperidine-1-carboxylate;
tert-butyl 4-(6-(4-methyl-3-sulfamoylphenylamino)-1H-pyrazolo[3,4-d]pyrimidin-1-yl)cyclohexylcarbamate;
5-(1-((cis-4-aminocyclohexyl)methyl)-1H-pyrazolo[3,4-d]pyrimidin-6-ylamino)-2-methylbenzenesulfonamide;
5-(1-(((1R,4R)-4-(aminomethyl)cyclohexyl)methyl)-1H-pyrazolo[3,4-d]pyrimidin-6-ylamino)-2-methylbenzenesulfonamide;
1-(((1R,4R)-4-(aminomethyl)cyclohexyl)methyl)-N-(4-(4-methylpiperazin-1-yl)phenyl)-1H-pyrazolo[3,4-d]pyrimidin-6-amine;
1-(((1R,4R)-4-aminocyclohexyl)methyl)-N-(4-(4-methylpiperazin-1-yl)phenyl)-1H-pyrazolo[3,4-d]pyrimidin-6-amine;
2-methyl-5-(1-(piperidin-4-yl)-1H-pyrazolo[3,4-d]pyrimidin-6-ylamino)benzenesulfonamide;
N-(4-(4-methylpiperazin-1-yl)phenyl)-1-(piperidin-4-yl)-1H-pyrazolo[3,4-d]pyrimidin-6-amine;
5-(1-(4-aminocyclohexyl)-1H-pyrazolo[3,4-d]pyrimidin-6-ylamino)-2-methylbenzenesulfonamide;
1-(((1S,4S)-4-aminocyclohexyl)methyl)-1H-pyrazolo[3,4-d]pyrimidin-6-amine;
1-(((1R,4R)-4-aminocyclohexyl)methyl)-N-(1-methyl-1H-pyrazol-4-yl)-1H-pyrazolo[3,4-d]pyrimidin-6-amine;
2-(4-(1-(((1R,4R)-4-aminocyclohexyl)methyl)-1H-pyrazolo[3,4-d]pyrimidin-6-ylamino)-1H-pyrazol-1-yl)propan-1-ol;
N-(cis-4-((6-(4-Methyl-3-sulfamoylphenylamino)-1H-pyrazolo[3,4-d]pyrimidin-1-yl)methyl)cyclohexyl)acetamide;
N-(5-1-(((1S,4S)-4-(3,3-dimethylbutanamido)cyclohexyl)methyl)-1H-pyrazolo[3,4-d]pyrimidin-6-ylamino)-2-methylphenylsulfonyl)-3,3-dimethylbutanamide;
3,3-dimethyl-N-((1S,4S)-4-(6-(4-methyl-3-sulfamoylphenylamino)-1H-pyrazolo[3,4-d]pyrimidin-1-yl)methyl)cyclohexyl)butanamide;
3-((1-(cyclohexylmethyl)-1H-pyrazolo[3,4-d]pyrimidin-6-yl)methyl)benzenesulfonamide;
3-((1-(cyclohexylmethyl)-1H-pyrazolo[3,4-d]pyrimidin-6-yl)methyl)benzenesulfonamide;
N-(1-cyclohexylmethyl-1H-pyrazolo[3,4-d]pyrimidin-6-yl)-3-(1-cyclohexylmethyl-1H-pyrazolo[3,4-d]pyrimidin-6-ylmethyl)-benzenesulfonamide;
1-(cyclohexylmethyl)-N-(4-(4-methylpiperazin-1-yl)phenyl)-1H-pyrazolo[3,4-d]pyrimidin-6-amine;
tert-butyl ((1R,4R)-4-((6-(4-cyclohexylphenylamino)-1H-pyrazolo[3,4-d]pyrimidin-1-yl)methyl)cyclohexyl)methylcarbamate;
1-(((1R,4R)-4-(aminomethyl)cyclohexyl)methyl)-N-(4-cyclohexylphenyl)-1H-pyrazolo[3,4-d]pyrimidin-6-amine;
4-(1-(((1R,4R)-4-aminocyclohexyl)methyl)-1H-pyrazolo[3,4-d]pyrimidin-6-ylamino)-N,N-dimethylbenzenesulfonamide;
4-(1-(((1R,4R)-4-aminocyclohexyl)methyl)-1H-pyrazolo[3,4-d]pyrimidin-6-ylamino)-N-cyclopropylbenzenesulfonamide;
3-(1-(((1R,4R)-4-aminocyclohexyl)methyl)-1H-pyrazolo[3,4-d]pyrimidin-6-ylamino)benzamide;
[1-(4-amino-cyclohexylmethyl)-1H-pyrazolo[3,4-d]pyrimidin-6-yl]-[4-(1,1-dioxo-thiomorpholin-4-yl)-phenyl]-amine;
1-(((1R,4R)-4-aminocyclohexyl)methyl)-N-(4-(methylsulfonyl)phenyl)-1H-pyrazolo[3,4-d]pyrimidin-6-amine;
2-(4-(1-(((1R,4R)-4-aminocyclohexyl)methyl)-1H-pyrazolo[3,4-d]pyrimidin-6-ylamino)phenylsulfonyl)ethanol;
4-(1-(((1R,4R)-4-aminocyclohexyl)methyl)-1H-pyrazolo[3,4-d]pyrimidin-6-ylamino)-N-(pyridin-3-ylmethyl)benzenesulfonamide;
4-(1-(((1R,4R)-4-aminocyclohexyl)methyl)-1H-pyrazolo[3,4-d]pyrimidin-6-ylamino)-N-(4-methoxyphenyl)benzenesulfonamide;
4-(1-(pyridin-3-ylmethyl)-1H-pyrazolo[3,4-d]pyrimidin-6-ylamino)benzenesulfonamide;
N-(4-(4-methylpiperazin-1-yl)phenyl)-1-(pyridin-3-ylmethyl)-1H-pyrazolo[3,4-d]pyrimidin-6-amine;
[4-(1,1-dioxo-thiomorpholin-4-yl)-phenyl]-(1-pyridin-3-ylmethyl-1H-pyrazolo[3,4-d]pyrimidin-6-yl)-amine;
N1-(3-chlorophenyl)-N4-(1-(pyridin-3-ylmethyl)-1H-pyrazolo[3,4-d]pyrimidin-6-yl)benzene-1,4-diamine;
2-methyl-5-(4-(1-phenyl-1H-pyrazolo[3,4-d]pyrimidin-6-ylamino)phenylamino)benzenesulfonamide;
N1-(2-methoxyphenyl)-N4-(1-(pyridin-2-yl)-1H-pyrazolo[3,4-d]pyrimidin-6-yl)benzene-1,4-diamine;
2-(6-(4-(2-methoxyphenylamino)phenylamino)-1H-pyrazolo[3,4-d]pyrimidin-1-yl)-N-methylbenzenesulfonamide;
N1-(1-(cyclohexylmethyl)-1H-pyrazolo[3,4-d]pyrimidin-6-yl)-N4-phenylbenzene-1,4-diamine;
1-(cyclohexylmethyl)-N-(4-(morpholino sulfonyl)phenyl)-1H-pyrazolo[3,4-d]pyrimidin-6-amine; or
N1-(1-(cyclohexylmethyl)-1H-pyrazolo[3,4-d]pyrimidin-6-yl)-N4,N4-dimethylbenzene-1,4-diamine.

In a twentieth embodiment the invention provides a method of affecting hyperproliferative disorders in a patient comprising administering a therapeutically effective amount of a compound according to any of the foregoing embodiments or a physiologically acceptable salt, pro-drug or biologically active metabolites thereof to said patient.

In a twenty-first embodiment the invention provides a method of treating a condition in a patient comprising administering a therapeutically effective amount of a compound according to any of the foregoing embodiments or a physiologically acceptable salt, pro-drug or biologically active metabolites thereof to said patient, wherein said condition is rheumatoid arthritis, asthma, Crohn's disease, psoriasis, psoriatic arthritis, juvenile arthritis, juvenile idiopathic arthritis or cancer.

In a twenty-second embodiment the invention provides a method of any of the foregoing embodiments wherein the cancer is a solid tumor, a sarcoma, fibrosarcoma, osteoma, melanoma, retinoblastoma, a rhabdomyosarcoma, glioblastoma, neuroblastoma, teratocarcinoma, an hematopoietic malignancy, Kaposi's sarcoma, Hodgkin's disease, lymphoma, myeloma, leukemia or malignant ascites.

DETAILED DESCRIPTION OF THE INVENTION

Protein kinases are a broad and diverse class, of over 500 enzymes, that include oncogenes, growth factors receptors, signal transduction intermediates, apoptosis related kinases and cyclin dependent kinases. They are responsible for the transfer of a phosphate group to specific tyrosine, serine or threonine amino acid residues, and are broadly classified as tyrosine and serine/threonine kinases as a result of their substrate specificity.

The Jak family kinases (Jak1, Jak2, Jak3 and Tyk2) are cytoplasmic tyrosine kinases that associate with membrane bound cytokine receptors. Cytokine binding to their receptor initiates Jak kinase activation via trans and autophosphorylation processes. The activated Jak kinases phosphorylate residues on the cytokine receptors creating phosphotyrosine binding sites for SH2 domain containing proteins such as Signal Transduction Activators of Transcript (STAT) factors and other signal regulators transduction such as SOCS proteins and SHIP phosphatases. Activation of STAT factors via this process leads to their dimerization, nuclear translocation and new mRNA transcription resulting in expression of immunocyte proliferation and survival factors as well as additional cytokines, chemokines and molecules that facilitate cellular trafficking (see *Journal of Immunology*, 2007, 178, p. 2623). Jak kinases transduce signals for many different cytokine families and hence potentially play roles in diseases with widely different pathologies including but not limited to the following examples. Both Jak1 and Jak3 control signaling of the so-called common gamma chain cytokines (IL2, IL4, IL7, IL9, IL15 and IL21), hence simultaneous inhibition of either Jak1 or Jak3 could be predicted to impact Th1 mediated diseases such as rheumatoid arthritis via blockade of IL2, IL7 and IL15 signaling. On the other hand, IL2 signaling has recently been shown to be essential for development and homeostasis of T-regulatory cells (Malek T R et al., *Immunity*, 2002, 17(2), p. 167-78). Thus, based on genetic data, blockade of IL2 signaling alone is predicted to result in autoimmunity (Yamanouchi J et al., *Nat. Genet.*, 2007, 39(3), p. 329-37, and Willerford D M et al., *Immunity*, 1995, 3(4), p. 521-30). Th2 mediated diseases such as asthma or atopic dermatitis via IL4 and IL9 signaling blockade. Jak1 and Tyk2 mediate signaling of IL13 (see Int. Immunity, 2000, 12, p. 1499). Hence, blockade of these may also be predicted to have a therapeutic effect in asthma. These two kinases are also thought to mediate Type I interferon signaling; their blockade could therefore be predicted to reduce the severity of systemic lupus erythematosus (SLE). Tyk2 and Jak2 mediate signaling of IL12 and IL23. In fact, blockade of these cytokines using monoclonal antibodies has been effective in treating psoriasis. Therefore blockade of this pathway using inhibitors of these kinases could be predicted to be effective in psoriasis as well. In summary, this invention describes small-molecule compounds that inhibit, regulate and/or modulate Jak family kinase activity that is pivotal to several mechanisms thought critical to the progression of autoimmune diseases including, but not limited to, rheumatoid arthritis (RA), systemic lupus erythematosus (SLE), multiple sclerosis (MS), Crohn's disease, psoriasis and asthma.

Several pathologically significant cytokines signal via Jak1 alone (Guschin D, et al., *EMBO J.* 1995 Apr. 3; 14(7): 1421-9; Parganas E, et al., *Cell.* 1998 May 1; 93(3):385-95; Rodig S. J., et al., *Cell.* 1998 May 1; 93(3):373-83). Blockade of one of these, IL6, using an IL6R neutralizing antibody, has been shown to significantly improve disease scores in human rheumatoid arthritis patients (Nishimoto N. et al., *Ann Rheum Dis.*, 2007, 66(9), p. 1162-7). Similarly, blockaded of GCSF signaling, which is also mediated by Jak1 alone, using neutralizing monoclonal antibodies or target gene deletion protects mice from experimental arthritis (Lawlor K. E. et al., *Proc Natl Acad Sci U.S.A.*, 2004, 101(31), p. 11398-403). Accordingly, the identification of small-molecule compounds that inhibit, regulate and/or modulate the signal transduction of kinases, such as Jak1, is a desirable means to prevent or treat autoimmune diseases or other diseases related to abberant Jak1 function.

Jak2 is also activated in a wide variety of human cancers such as prostate, colon, ovarian and breast cancers, melanoma, leukemia and other haematopoietic malignancies. In addition, somatic point mutation of the Jak2 gene has been identified to be highly associated with classic myeloproliferative disorders (MPD) and infrequently in other myeloid disorders. Constitutive activation of Jak2 activity is also caused by chromosomal translocation in hematopoeitic malignancies. It has also been shown that inhibition of the Jak/STAT pathway, and in particular inhibition of Jak2 activity, results in anti-proliferative and pro-apoptotic effects largely due to inhibition of phosphorylation of STAT. Furthermore, pharmacological modulation or inhibition of Jak2 activity could effectively block tumor growth and induce apoptosis by reducing the STAT phosphorylation in cell culture and human tumor xenografts in vivo. Accordingly, the identification of small-molecule compounds that inhibit, regulate and/or modulate the signal transduction of kinases, particularly Jak2, is desirable as a means to treat or prevent diseases and conditions associated with cancers.

Jak kinases also transmit signals regulating essential physiological processes whose inhibition could be undesirable. For example Jak2 mediates the signaling of Erythropoetin (Epo) and Granulocyte/Monocyte-Colony Stimulating Factor. Individuals with genetic, congenital or acquired defects in these signaling pathways can develop potentially life-threatening complications such as anemia and neutrophil dysfunction. Accordingly, one non-limiting aspect of this invention also relates to a method to identify compounds that may have a favorable safety profile as a result of them selectively avoiding inhibition of Jak2.

The protein kinase C family is a group of serine/threonine kinases that comprises twelve related isoenzymes. Its members are encoded by different genes and are sub-classified according to their requirements for activation. The classical enzymes (cPKC) require diacylglycerol (DAG), phosphatidylserine (PS) and calcium for activation. The novel PKC's (nPKC) require DAG and PS but are calcium independent. The atypical PKC's (aPKC) do not require calcium or DAG.

PKCtheta is a member of the nPKC sub-family (Baier, G., et al., *J. Biol. Chem.*, 1993, 268, 4997). It has a restricted expression pattern, found predominantly in T cells and skeletal muscle (Mischak, H. et al., *FEBS Lett.*, 1993, 326, p. 51), with some expression reported in mast cells (Liu, Y. et al., *J. Leukoc. Biol.*, 2001, 69, p. 831) and endothelial cells (Mattila, P. et al., *Life Sci.*, 1994, 55, p. 1253).

Upon T cell activation, a supramolecular activation complex (SMAC) forms at the site of contact between the T cell and the antigen presenting cell (APC). PKCtheta is the only PKC isoform found to localize at the SMAC (Monks, C. et al., *Nature*, 1997, 385, 83), placing it in proximity with other signaling enzymes that mediate T cell activation processes.

In another study (Baier-Bitterlich, G. et al., *Mol. Cell. Biol.*, 1996, 16, 842) the role of PKCtheta in the activation of AP-1, a transcription factor important in the activation of the IL-2 gene, was confirmed. In unstimulated T cells, constitutively active PKCtheta stimulated AP-1 activity while in cells with dominant negative PKCtheta, AP-1 activity was not induced upon activation by PMA.

Other studies showed that PKCtheta, via activation of IκB kinase beta, mediates activation of NF-κB induced by T cell receptor/CD28 co-stimulation (N. Coudronniere et al., *Proc. Nat. Acad. Sci. U.S.A.*, 2000, 97, p. 3394; and Lin, X. et al., *Mol. Cell. Biol.*, 2000, 20, p. 2933).

Proliferation of peripheral T cells from PKCtheta knockout mice, in response to T cell receptor (TCR)/CD28 stimulation was greatly diminished compared to T cells from wild type mice. In addition, the amount of IL-2 released from the T cells was also greatly reduced (Sun, Z. et al., *Nature*, 2000, 404, p. 402). It has also been shown that PKCtheta-deficient mice show impaired pulmonary inflammation and airway hyperresponsiveness (AHR) in a Th2-dependent murine asthma model, with no defects in viral clearance and Th1-dependent cytotoxic T cell function (Berg-Brown, N. N. et al., *J. Exp. Med.*, 2004, 199, p. 743; Marsland, B. J. et al., *J. Exp. Med.*, 2004, 200, p. 181). The impaired Th2 cell response results in reduced levels of IL-4 and immunoglobulin E (IgE), contributing to the AHR and inflammatory pathophysiology. Otherwise, the PKCtheta knockout mice seemed normal and fertile.

Evidence also exists that PKCtheta participates in the IgE receptor (FcεRI)-mediated response of mast cells (Liu, Y. et al., *J. Leukoc. Biol.*, 2001, 69, p. 831). In human-cultured mast cells (HCMC), it has been demonstrated that PKC kinase activity rapidly localizes to the membrane following FcεRI cross-linking (Kimata, M. et al., *Biochem. Biophys. Res. Commun.*, 1999, 257(3), p. 895). A recent study examining in vitro activity of bone marrow mast cells (BMMC) derived from wild-type and PKCtheta-deficient mice shows that upon FceRI cross linking, BMMCs from PKCtheta-deficient mice reduced levels of IL-6, tumor necrosis factor-alpha (TNFα) and IL-13 in comparison with BMMCs from wild-type mice, suggesting a potential role for PKCtheta in mast cell cytokine production in addition to T cell activation (Ciarletta, A. B. et al., poster presentation at the 2005 American Thoracic Society International Conference).

The studies cited above and others studies confirm the critical role of PKCtheta in T cells activation and in mast cell (MC) signaling. Thus an inhibitor of PKCtheta would be of therapeutic benefit in treating immunological disorders and other diseases mediated by the inappropriate activation of T cells and MC signaling.

Mitosis is a process by which a complete copy of a duplicated genome is segregated by the microtubule spindle apparatus into two daughter cells. Aurora-kinases, key mitotic regulators required for genome stability, have been found to be overexpressed in human tumors. There is therefore an existing need in the therapeutic arts for compounds which inhibit Aurora-kinases, compositions comprising the inhibitors and methods of treating diseases during which Aurora-kinases are unregulated or overexpressed.

The reversible phosphorylation of proteins is one of the primary biochemical mechanisms mediating eukaryotic cell signaling. This reaction is catalyzed by protein kinases that transfer the γ-phosphate group of ATP to hydroxyl groups on target proteins. 518 such enzymes exist in the human genome of which ~90 selectively catalyze the phosphorylation of tyrosine hydroxyl groups. Cytosolic tyrosine kinases reside intracellularly whereas receptor tyrosine kinases (RTKs) possess both extracellular and intracellular domains and function as membrane spanning cell surface receptors. As such, RTKs mediate the cellular responses to environmental signals and facilitate a broad range of cellular processes including proliferation, migration and survival.

RTK signaling pathways are normally highly regulated, yet their over-activation has been shown to promote the growth, survival and metastasis of cancer cells. Dysregulated RTK signaling occurs through gene over-expression or mutation and has been correlated with the progression of various human cancers.

The VEGF receptor (VEGFR) family consists of three RTKs, KDR (kinase insert domain-containing receptor; VEGFR2), FLT1 (Fms-like tyrosine kinase; VEGFR1), and FLT4 (VEGFR3). These receptors mediate the biological function of the vascular endothelial growth factors (VEGF-A, -B, -C, -D, -E and placenta growth factor (PlGF)), a family of homodimeric glycoproteins that bind the VEGF receptors with varying affinities.

KDR is the major mediator of the mitogenic, angiogenic and permeability-enhancing effects of VEGF-A, hereafter referred to as VEGF. Many different cell types are able to produce VEGF, yet its biological activity is limited predominately to the vasculature by way of the endothelial cell-selective expression of KDR. Not surprisingly, the VEGF/KDR axis is a primary mediator of angiogenesis, the means by which new blood vessels are formed from preexisting vessels.

FLT1 binds VEGF, VEGF-B and placental growth factor. FLT1 is expressed on the surface of smooth muscle cells, monocytes and hematopoietic stems cells in addition to endothelial cells. Activation of FLT1 signaling results in the mobilization of marrow-derived endothelial progenitor cells that are recruited to tumors where they contribute to new blood vessel formation.

FLT4 mediates the signaling of VEGF-C and VEGF-D, which mediate formation of tumor-associated lymphatic vessels (lymphangiogenesis). Lymphatic vessels are one of the routes by which cancer cells disseminate from solid tumors during metastasis.

The PDGF receptor (PDGFR) family consists of five RTK's, PDGFR-a and -b, CSF1R, KIT, and FLT3.

The a and b isoforms of the platelet-derived growth factor (PDGF) receptors occur as homodimers or a/b heterodimers and are found most commonly on the surface of fibroblasts and smooth muscle cells. PDGFR-b contributes to tumor angiogenesis through the proliferation and migration of pericytes, the peri-endothelial cells that associate with and stabilize immature blood vessels. In gliomas, autocrine PDGFR stimulation, brought about by the co-expression of PDGF and PDGF receptors, mediates tumor cell proliferation and survival.

CSF-1R is encoded by the cellular homolog of the retroviral oncogene v-fms and is a major regulator of macrophage development. Macrophages are frequent components of tumor stroma and have been shown to modify the extracellular matrix in a manner beneficial to tumor growth and metastasis.

KIT is expressed by hematopoietic progenitor cells, mast cells, germ cells and by pacemaker cells in the gut (interstitial cells of Cajal). It contributes to tumor progression by two general mechanisms namely autocrine stimulation by its ligand, stem cell factor (SCF), and through mutations that result in ligand-independent kinase activity.

FLT3 is normally expressed on hematopoietic stem cells where its interaction with FLT3 ligand (FL) stimulates stem cell survival, proliferation and differentiation. In addition to being over-expressed in various leukemia cells, FLT3 is frequently mutated in hematological malignancies with approximately one-third of patients with acute myeloid leukemia (AML) harboring activating mutations.

Many of the kinases, whether a receptor or non-receptor tyrosine kinase or a S/T kinase have been found to be involved in cellular signaling pathways involved in numerous pathogenic conditions, including immunomodulation, inflammation, or proliferative disorders such as cancer.

Many autoimmune diseases and disease associated with chronic inflammation, as well as acute responses, have been linked to excessive or unregulated production or activity of one or more cytokines.

Many autoimmune diseases and disease associated with chronic inflammation, as well as acute responses, have been linked to excessive or unregulated production or activity of one or more cytokines. The present compounds are useful in the treatment of inflammatory disorders including, but not limited to rheumatoid arthritis, psoriatic arthritis, inflammatory bowel disease, Crohn's disease, lupus, multiple sclerosis, juvenile chronic arthritis, Lyme arthritis, reactive arthritis, septic arthritis, ankylosing spondylitis, spondyloarthropathy and systemic lupus erythematosus.

The compounds of the invention are also useful in the treatment of cardiovascular disorders, such as acute myocardial infarction, acute coronary syndrome, chronic heart failure, myocardial infarction, atherosclerosis, viral myocarditis, cardiac allograft rejection, and sepsis-associated cardiac dysfunction. Furthermore, the compounds of the present invention are also useful for the treatment of central nervous system disorders such as meningococcal meningitis, Alzheimer's disease and Parkinson's disease.

The compounds of the invention are also useful in the treatment of rheumatoid arthritis, an ocular condition, a cancer, a solid tumor, a sarcoma, fibrosarcoma, osteoma, melanoma, retinoblastoma, a rhabdomyosarcoma, glioblastoma, neuroblastoma, teratocarcinoma, hypersensitivity reactions, hyperkinetic movement disorders, hypersensitivity pneumonitis, hypertension, hypokinetic movement disorders, aordic and peripheral aneuryisms, hypothalamic-pituitary-adrenal axis evaluation, aortic dissection, arterial hypertension, arteriosclerosis, arteriovenous fistula, ataxia, spinocerebellar degenerations, streptococcal myositis, structural lesions of the cerebellum, subacute sclerosing panencephalitis, syncope, syphilis of the cardiovascular system, systemic anaphalaxis, systemic inflammatory response syndrome, systemic onset juvenile rheumatoid arthritis, T-cell or FAB ALL, Telangiectasia, thromboangitis obliterans, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, atrial fibrillation (sustained or paroxysmal), atrial flutter, atrioventricular block, B cell lymphoma, bone graft rejection, bone marrow transplant (BMT) rejection, small bowel transplant rejection, spinal ataxia, lymphoma, myeloma, leukaemia, malignant ascites, hematopoietic cancers, a diabetic condition such as insulin-dependent diabetes mellitus glaucoma, diabetic retinopathy or microangiopathy, sickle cell anaemia, chronic inflammation, synovitis, glomerulonephritis, graft rejection, Lyme disease, von Hippel Lindau disease, pemphigoid, Paget's disease, fibrosis, sarcoidosis, cirrhosis, thyroiditis, hyperviscosity syndrome, Osler-Weber-Rendu disease, chronic occlusive pulmonary disease, asthma or edema following burns, trauma, radiation, stroke, hypoxia, ischemia, ovarian hyperstimulation syndrome, post perfusion syndrome, post pump syndrome, post-MI cardiotomy syndrome, preeclampsia, menometrorrhagia, endometriosis, pulmonary hypertension, infantile hemangioma, or infection by Herpes simplex, Herpes Zoster, human immunodeficiency virus, parapoxvirus, protozoa or toxoplasmosis, progressive supranucleo palsy, primary pulmonary hypertension, radiation therapy, Raynaud's phenomenon, Raynaud's disease, Refsum's disease, regular narrow QRS tachycardia, renovascular hypertension, restrictive cardiomyopathy, sarcoma, senile chorea, senile dementia of Lewy body type, shock, skin allograft, skin changes syndrome, ocular or macular edema, ocular neovascular disease, scleritis, radial keratotomy, uveitis, vitritis, myopia, optic pits, chronic retinal detachment, post-laser treatment complications, conjunctivitis, Stargardt's disease, Eales disease, retinopathy, macular degeneration, restenosis, ischemia/reperfusion injury, ischemic stroke, vascular occlusion, carotid obstructive disease, ulcerative colitis, inflammatory bowel disease, diabetes, diabetes mellitus, insulin dependent diabetes mellitus, allergic diseases, dermatitis scleroderma, graft versus host disease, organ transplant rejection (including but not limited to bone marrow and solid organ rejection), acute or chronic immune disease associated with organ transplantation, sarcoidosis, disseminated intravascular coagulation, Kawasaki's disease, nephrotic syndrome, chronic fatigue syndrome, Wegener's granulomatosis, Henoch-Schoenlein purpurea, microscopic vasculitis of the kidneys, chronic active hepatitis, septic shock, toxic shock syndrome, sepsis syndrome, cachexia, infectious diseases, parasitic diseases, acquired immunodeficiency syndrome, acute transverse myelitis, Huntington's chorea, stroke, primary biliary cirrhosis, hemolytic anemia, malignancies, Addison's disease, idiopathic Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, chlamydia, yersinia and salmonella associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, peripheral vascular disorders, peritonitis, pernicious anemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis A, Hepatitis B, Hepatitis C, His bundle arrythmias, HIV infection/HIV neuropathy, common varied immunodeficiency (common variable hypogammaglobulinaemia), dilated cardiomyopathy, female infertility, ovarian failure, premature ovarian failure, fibrotic lung disease, chronic wound healing, cryptogenic fibrosing alveolitis, post-inflammatory interstitial lung disease, interstitial pneumonitis, pneumocystis carinii pneumonia, pneumonia, connective tissue disease associated interstitial lung disease, mixed connective tissue disease, associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthritis, primary sclerosing cholangitis, psoriasis type 1, psoriasis type 2, idiopathic leucopaenia, autoimmune neutropaenia, renal disease NOS, glomerulonephritides, microscopic vasculitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, acute and chronic pain (different forms of pain), Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopaenia, toxicity, transplants, and diseases involving inappropriate vascularization for example diabetic retinopathy, retinopathy of prematurity, choroidal neovascularization due to age-related macular degeneration, and infantile hemangiomas in human beings. In addition, such compounds may be useful in the treatment of disorders such as ascites, effusions, and exudates, including for example macular edema, cerebral edema, acute lung injury, adult respiratory distress syndrome (ARDS), proliferative disorders such as restenosis, fibrotic disorders such as hepatic cirrhosis and atherosclerosis, mesangial cell proliferative disorders such as diabetic nephropathy, malignant nephrosclerosis, thrombotic microangiopathy syndromes, and glomerulopathies, myocardial angiogenesis, coronary and cerebral collaterals, ischemic limb angiogenesis, ischemia/reperfusion injury, peptic ulcer *Helicobacter* related diseases, virally-induced angiogenic disorders, preeclampsia, menometrorrhagia, cat scratch fever, rubeosis, neovascular glaucoma and retinopathies such as those associated with diabetic retinopathy, retinopathy of prematurity, or age-related macular degeneration. In addition, these compounds can be used as active agents against hyperproliferative disorders such as thyroid hyperplasia (especially Grave's disease), and cysts (such as hypervascularity of ovarian stroma characteristic of polycystic ovarian syndrome (Stein-Leventhal syndrome) and polycystic kidney disease since such diseases require a proliferation of blood vessel cells for growth and/or metastasis.

Compounds of Formula (I) of the invention can be used alone or in combination with another therapeutic agent to treat such diseases. It should be understood that the compounds of the invention can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the compound of the present invention. The additional agent also can be an agent that imparts a beneficial attribute to the therapeutic composition e.g., an agent that affects the viscosity of the composition.

It should further be understood that the combinations which are to be included within this invention are those combinations useful for their intended purpose. The agents set forth below are illustrative for purposes and not intended to be limited. The combinations, which are part of this invention, can be the compounds of the present invention and at least one additional agent selected from the lists below. The combination can also include more than one additional agent, e.g., two or three additional agents if the combination is such that the formed composition can perform its intended function.

Preferred combinations are non-steroidal anti-inflammatory drug(s) also referred to as NSAIDS which include drugs like ibuprofen. Other preferred combinations are corticosteroids including prednisolone; the well known side-effects of steroid use can be reduced or even eliminated by tapering the steroid dose required when treating patients in combination with the compounds of this invention. Non-limiting examples of therapeutic agents for rheumatoid arthritis with which a compound of Formula (I) of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, and PDGF. S/T kinase inhibitors of the invention can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists like chimeric, humanized or human TNF antibodies, D2E7 (U.S. Pat. No. 6,090,382, HUMIRA™), CA2 (REMICADE™), CDP 571, and soluble p55 or p75 TNF receptors, derivatives, thereof, (p75TNFR1gG (ENBREL™) or p55TNFR1gG (Lenercept), and also TNFα converting enzyme (TACE) inhibitors; similarly IL-1 inhibitors (Interleukin-1-converting enzyme inhibitors, IL-1RA etc.) may be effective for the same reason. Other preferred combinations include Interleukin 11. Yet other preferred combinations are the other key players of the autoimmune response which may act parallel to, dependent on or in concert with IL-18 function; especially preferred are IL-12 antagonists including IL-12 antibodies or soluble IL-12 receptors, or IL-12 binding proteins. It has been shown that IL-12 and IL-18 have overlapping but distinct functions and a combination of antagonists to both may be most effective. Yet another preferred combination is non-depleting anti-CD4 inhibitors. Yet other preferred combinations include antagonists of the co-stimulatory pathway CD80 (B7.1) or CD86 (B7.2) including antibodies, soluble receptors or antagonistic ligands. A compound of Formula (I) of the invention may also be combined with agents, such as methotrexate, 6-MP, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), statins (for example: atorvastatin, simvastatin, lovastatin, rosuvastatin, pitavastatin, fluvastatin and pravastatin), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™ and p55TNFRIgG (Lenercept), sIL-1RI, sIL-1RII, sIL-6R), antiinflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, and Mesopram. Preferred combinations include methotrexate or leflunomide and in moderate or severe rheumatoid arthritis cases, cyclosporine and anti-TNF antibodies as noted above.

Non-limiting examples of therapeutic agents for inflammatory bowel disease with which a compound of Formula (I) of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g. NIK, IKK, or MAP kinase inhibitors); IL-1β converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ). Preferred examples of therapeutic agents for Crohn's disease with which a compound of Formula (I) can be combined include the following: TNF antagonists, for example, anti-TNF antibodies, D2E7 (U.S. Pat. No. 6,090,382, HUMIRA™), CA2 (REMICADE™), CDP 571, TNFR-Ig constructs, (p75TNFRIgG (ENBREL™) and p55TNFRIgG (LENERCEPT™)) inhibitors and PDE4 inhibitors. A compound of Formula (I) can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors 6-mercaptopurines; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of Formula (I) can be combined include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BE-TASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; clabribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of Formula (I) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGFβ).

Preferred examples of therapeutic agents for multiple sclerosis in which a compound of Formula (I) can be combined to include interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

A compound of Formula (I) may also be combined with agents, such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis with which a compound of Formula (I) can be combined include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, and anti-TNF antibodies, D2E7 (U.S. Pat. No. 6,090,382; HUMIRA™), CA2 (REMICADE™), CDP 571, TNFR-Ig constructs, (p75TNFRIgG (ENBREL™) and p55TNFRIgG (LENERCEPT™)

Non-limiting examples of therapeutic agents for asthma with which a compound of Formula (I) can be combined include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, anti-IL-13 antibody, and metaproterenol sulfate.

Non-limiting examples of therapeutic agents for COPD with which a compound of Formula (I) can be combined include the following: Letairis™, albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast and roflumilast.

Non-limiting examples of therapeutic agents for HCV with which a compound of Formula (I) can be combined include the following: Interferon-alpha-2α, Interferon-alpha-2β, Interferon-alpha con1, Interferon-alpha-n1, pegylated interferon-alpha-2α, pegylated interferon-alpha-2β, ribavirin, peginterferon alfa-2b+ribavirin, ursodeoxycholic acid, glycyrrhizic acid, thymalfasin, Maxamine, VX-497 and any compounds that are used to treat HCV through intervention with the following targets: HCV polymerase, HCV protease, HCV helicase, and HCV IRES (internal ribosome entry site).

Non-limiting examples of therapeutic agents for Idiopathic Pulmonary Fibrosis with which a compound of Formula (I) can be combined include the following: prednisone, azathioprine, albuterol, colchicine, albuterol sulfate, digoxin, gamma interferon, methylprednisolone sod succ, lorazepam, furosemide, lisinopril, nitroglycerin, spironolactone, cyclophosphamide, ipratropium bromide, actinomycin d, alteplase, fluticasone propionate, levofloxacin, metaproterenol sulfate, morphine sulfate, oxycodone HCl, potassium chloride, triamcinolone acetonide, tacrolimus anhydrous, calcium, interferon-alpha, methotrexate, mycophenolate mofetil and interferon-gamma-1β.

Non-limiting examples of therapeutic agents for myocardial infarction with which a compound of Formula (I) can be combined include the following: aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril HCl/mag carb, bumetanide, alteplase, enalaprilat, amiodarone hydrochloride, tirofiban HCl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine HCl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, and cariporide.

Non-limiting examples of therapeutic agents for psoriasis with which a compound of Formula (I) can be combined include the following: D2E7 (U.S. Pat. No. 6,090,382, HUMIRA™), calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, he/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, and sulfasalazine.

Non-limiting examples of therapeutic agents for psoriatic arthritis with which a compound of Formula (I) can be combined include the following: D2E7 (U.S. Pat. No. 6,090,382, HUMIRA™), methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept and efalizumab.

Non-limiting examples of therapeutic agents for restenosis with which a compound of Formula (I) can be combined include the following: sirolimus, paclitaxel, everolimus, tacrolimus, ABT-578, Letairis™ and acetaminophen.

Non-limiting examples of therapeutic agents for sciatica with which a compound of Formula (I) can be combined include the following: hydrocodone bitartrate/apap, rofecoxib, cyclobenzaprine HCl, methylprednisolone, naproxen, ibuprofen, oxycodone HCl/acetaminophen, celecoxib, valdecoxib, methylprednisolone acetate, prednisone, codeine phosphate/apap, tramadol hcl/acetaminophen, metaxalone, meloxicam, methocarbamol, lidocaine hydrochloride, diclofenac sodium, gabapentin, dexamethasone, carisoprodol, ketorolac tromethamine, indomethacin, acetaminophen, diazepam, nabumetone, oxycodone HCl, tizanidine HCl, diclofenac sodium/misoprostol, propoxyphene napsylate/apap, asa/oxycod/oxycodone ter, ibuprofen/hydrocodone bit, tramadol HCl, etodolac, propoxyphene HCl, amitriptyline HCl, carisoprodol/codeine phos/asa, morphine sulfate, multivitamins, naproxen sodium, orphenadrine citrate, and temazepam.

Preferred examples of therapeutic agents for SLE (Lupus) with which a compound of Formula (I) can be combined include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of Formula (I) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of Formula (I) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of Formula (I) can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of Formula (I) may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (U.S. Pat. No. 6,090,382; HUMIRA™), CA2 (REMICADE™), SIMPONI™ (golimumab), CIMZIA™, ACTEMRA™, CDP 571, TNFR-Ig constructs, (p75TNFRIgG (ENBREL™) and p55TNFRIgG (Lenercept™).

In this invention, the following definitions are applicable:

A "therapeutically effective amount" is an amount of a compound of Formula (I) or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

"Pharmaceutically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphoric acid, methanesulfonic acid, ethanesulfonic acid, p-toluenesulfonic acid, citric acid, fumaric acid, maleic acid, succinic acid, benzoic acid, salicylic acid, lactic acid, tartaric acid (e.g. (+) or (−)-tartaric acid or mixtures thereof), amino acids (e.g. (+) or (−)-amino acids or mixtures thereof), and the like. These salts can be prepared by methods known to those skilled in the art.

Certain compounds of Formula (I) which have acidic substituents may exist as salts with pharmaceutically acceptable bases. The present invention includes such salts. Examples of such salts include sodium salts, potassium salts, lysine salts and arginine salts. These salts may be prepared by methods known to those skilled in the art.

Certain compounds of Formula (I) and their salts may exist in more than one crystal form and the present invention includes each crystal form and mixtures thereof.

Certain compounds of Formula (I) and their salts may also exist in the form of solvates, for example hydrates, and the present invention includes each solvate and mixtures thereof.

Certain compounds of Formula (I) may contain one or more chiral centers, and exist in different optically active forms. When compounds of Formula (I) contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of Formula (I) contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of Formula (I), and mixtures thereof.

Certain compounds of Formula (I) may exist in different tautomeric forms or as different geometric isomers, and the present invention includes each tautomer and/or geometric isomer of compounds of Formula (I) and mixtures thereof.

Certain compounds of Formula (I) may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Formula (I) and mixtures thereof.

Certain compounds of Formula (I) may exist in zwitterionic form and the present invention includes each zwitterionic form of compounds of Formula (I) and mixtures thereof.

As used herein the term "pro-drug" refers to an agent which is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents wherein the free hydrogen is replaced by $(C_1-C_4)$alkyl, $(C_2-C_{12})$alkanoyloxymethyl, $(C_4-C_9)$1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$-alkylcarbamoyl-$(C_1-C_2)$alkyl and piperidino-, pyrrolidino- or morpholino$(C_2-C_3)$ alkyl.

Other exemplary pro-drugs release an alcohol of Formula (I) wherein the free hydrogen of the hydroxyl substituent (e.g., $R^1$ contains hydroxyl) is replaced by $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylamino-methyl, succinoyl, $(C_1-C_6)$alkanoyl, α-amino$(C_1-C_4)$alkanoyl, arylactyl and α-aminoacyl, or α-aminoacyl-α-aminoacyl wherein said α-aminoacyl moieties are independently any of the naturally occurring L-amino acids found in proteins, $P(O)(OH)_2$, —$P(O)(O(C_1-C_6)alkyl)_2$ or glycosyl (the radical resulting from detachment of the hydroxyl of the hemiacetal of a carbohydrate).

As used herein, the term "bridged $(C_5-C_{12})$cycloalkyl group" means a saturated or unsaturated, bicyclic, spirocyclic, or polycyclic bridged hydrocarbon group having two or three $C_3-C_{10}$ cycloalkyl rings. Non bridged cycloalkyls are excluded. Bridged cyclic hydrocarbon groups may include such as bicyclo[2.1.1]hexyl, bicyclo[2.2.1]heptyl, bicyclo [2.2.2]octyl, bicyclo[4.3.1]decyl, bicyclo[3.3.1]nonyl, bornyl, bornenyl, norbornyl, norbornenyl, 6,6-dimethylbicyclo[3.1.1]heptyl, tricyclobutyl, and adamantyl.

As used herein the term "bridged $(C_2-C_{10})$ heterocyclyl" means bicyclic, spirocyclic, or polycyclic aza-bridged hydrocarbon groups and may include azanorbornyl, quinuclidinyl, isoquinuclidinyl, tropanyl, azabicyclo[3.2.1]octanyl, azabicyclo[2.2.1]heptanyl, 2-azabicyclo[3.2.1]octanyl, azabicyclo [3.2.1]octanyl, azabicyclo[3.2.2]nonanyl, azabicyclo[3.3.0] nonanyl, and azabicyclo[3.3.1]nonanyl, preferably tropanyl, 2-oxa-5-azabicyclo[2.2.1]hept-5-yl.

The term "heterocyclic" or "heterocyclyl", as used herein, include non-aromatic, ring systems, including, but not limited to, monocyclic, bicyclic and tricyclic rings, which can be completely saturated or which can contain one or more units of unsaturation, for the avoidance of doubt, the degree of unsaturation does not result in an aromatic ring system) and have 5 to 12 atoms including at least one heteroatom, such as nitrogen, oxygen, or sulfur. For purposes of exemplification, which should not be construed as limiting the scope of this invention, the following are examples of heterocyclic rings: azepinyl, azetidinyl, indolinyl, isoindolinyl, morpholinyl, piperazinyl, piperidinyl, pyrrolidinyl, quinucludinyl, thiomorpholinyl, tetrahydropyranyl, tetrahydrofuranyl, tetrahydroindolyl, thiomorpholinyl and tropanyl.

The term "heteroaryl" as used herein, include aromatic ring systems, including, but not limited to, monocyclic, bicyclic and tricyclic rings, and have 5 to 12 atoms including at least one heteroatom, such as nitrogen, oxygen, or sulfur. For purposes of exemplification, which should not be construed as limiting the scope of this invention: azaindolyl, benzo(b) thienyl, benzimidazolyl, benzofuranyl, benzoxazolyl, benzothiazolyl, benzothiadiazolyl, benzoxadiazolyl, furanyl, imidazolyl, imidazopyridinyl, indolyl, indazolyl, isoxazolyl, isothiazolyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrazolyl, thiadiazolyl, or thienyl.

An "heterocycloalkyl" group, as used herein, is a heterocyclic group that is linked to a compound by an aliphatic group having from one to about eight carbon atoms. For example, a heterocycloalkyl group is a morpholinomethyl group.

As used herein, "alkyl" or notations such as "$(C_0-C_8)$" include straight chained or branched hydrocarbons which are completely saturated. When the group is a $C_0$ it means that the carbon atom is not present or in other words, it is a bond. Examples of alkyls and aliphatics are methyl, ethyl, propyl, isopropyl, butyl, pentyl, hexyl and isomers thereof. As used herein, "alkenyl" and "alkynyl" means $C_2-C_8$ and includes straight chained or branched hydrocarbons which contain one or more units of unsaturation, one or more double bonds for alkenyl and one or more triple bonds for alkynyl.

As used herein, "aromatic" groups (or "aryl" groups) include aromatic carbocyclic ring systems (e.g. phenyl and cyclopentyldienyl) and fused polycyclic aromatic ring systems (e.g. naphthyl, biphenylenyl and 1,2,3,4-tetrahydronaphthyl).

As used herein, "cycloalkyl" means $C_3-C_{12}$ monocyclic or multicyclic (e.g., bicyclic, tricyclic, spirocyclic, etc.) hydrocarbons that are completely saturated or have one or more unsaturated bonds but do not amount to an aromatic group. Examples of a cycloalkyl group are cyclopropyl, cyclobutyl, cyclopentyl, cyclopentenyl, cyclohexyl and cyclohexenyl.

As used herein, many moieties or substituents are termed as being either "substituted" or "optionally substituted". When a moiety is modified by one of these terms, unless otherwise noted, it denotes that any portion of the moiety that is known to one skilled in the art as being available for substitution can be substituted, which includes one or more substituents, where if more than one substituent then each substituent is independently selected. Such means for substitution are well-known in the art and/or taught by the instant disclosure. For purposes of exemplification, which should not be construed as limiting the scope of this invention, some examples of groups that are substituents are: $(C_1-C_8)$alkyl groups, $(C_2-C_8)$alkenyl groups, $(C_2-C_8)$alkynyl groups, $(C_3-C_{10})$cycloalkyl groups, halogen (F, Cl, Br or I), halogenated $(C_1-C_8)$alkyl groups (for example but not limited to —$CF_3$), —O—$(C_1-C_8)$alkyl groups, —OH, —S—$(C_1-C_8)$alkyl groups, —SH, —NH$(C_1-C_8)$alkyl groups, —N(($C_1-C_8$) alkyl)$_2$ groups, —$NH_2$, —C(O)$NH_2$, —C(O)NH$(C_1-C_8)$ alkyl groups, —C(O)N(($C_1-C_8$)alkyl)$_2$, —NHC(O)H, —NHC(O) $(C_1-C_8)$alkyl groups, —N(($C_1-C_8$)alkyl)C(O)H, —N(($C_1-C_8$)alkyl)C(O)$(C_1-C_8)$alkyl groups, —NHC(O) $NH_2$, —NHC(O)NH$(C_1-C_8)$alkyl groups, —N(($C_1-C_8$) alkyl)C(O)$NH_2$ groups, —NHC(O)N(($C_1-C_8$)alkyl)$_2$ groups, —N(($C_1-C_8$)alkyl)C(O)N(($C_1-C_8$)alkyl)$_2$ groups, —N(($C_1-C_8$)alkyl)C(O)NH(($C_1-C_8$)alkyl), —C(O)H, —C(O)$(C_1-C_8)$ alkyl groups, —CN, —$NO_2$, —S(O)$(C_1-C_8)$alkyl groups, —S(O)$_2(C_1-C_8)$alkyl groups, —S(O)$_2$N(($C_1-C_8$)alkyl)$_2$ groups, —S(O)$_2$NH$(C_1-C_8)$alkyl groups, —S(O)$_2$$NH_2$ groups, —NHS(O)$_2(C_1-C_8)$alkyl groups, —N(($C_1-C_8$)alkyl)

S(O)$_2$(C$_1$-C$_8$)alkyl groups, —(C$_1$-C$_8$)alkyl-O—(C$_1$-C$_8$)alkyl groups, —O—(C$_1$-C$_8$)alkyl-O—(C$_1$-C$_8$)alkyl groups, —C(O)OH, —C(O)O(C$_1$-C$_8$)alkyl groups, NHOH, NHO(C$_1$-C$_8$)alkyl groups, —O-halogenated (C$_1$-C$_8$)alkyl groups (for example but not limited to —OCF$_3$), —S(O)$_2$-halogenated (C$_1$-C$_8$)alkyl groups (for example but not limited to —S(O)$_2$CF$_3$), —S-halogenated (C$_1$-C$_8$)alkyl groups (for example but not limited to —SCF$_3$), —(C$_1$-C$_6$) heterocycle (for example but not limited to pyrrolidine, tetrahydrofuran, pyran or morpholine), —(C$_1$-C$_6$) heteroaryl (for example but not limited to tetrazole, imidazole, furan or pyrazole), -phenyl, —NHC(O)O—(C$_1$-C$_6$)alkyl groups, —N((C$_1$-C$_6$)alkyl)C(O)O—(C$_1$-C$_6$)alkyl groups, —C(=NH)—(C$_1$-C$_6$)alkyl groups, —C(=NOH)—(C$_1$-C$_6$)alkyl groups, or —C(=N—O—(C$_1$-C$_6$)alkyl)-(C$_1$-C$_6$)alkyl groups.

One or more compounds of this invention can be administered to a human patient by themselves or in pharmaceutical compositions where they are mixed with biologically suitable carriers or excipient(s) at doses to treat or ameliorate a disease or condition as described herein. Mixtures of these compounds can also be administered to the patient as a simple mixture or in suitable formulated pharmaceutical compositions. A therapeutically effective dose refers to that amount of the compound or compounds sufficient to result in the prevention or attenuation of a disease or condition as described herein. Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds can be formulated for parenteral administration by injection, e.g. bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, methansulfonic, etc. Salts tend to be more soluble in aqueous or other protonic solvents than are the corresponding free base forms.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in a method of the present invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition of a given protein kinase activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p 1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50-90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the following Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared, for example, from the following ingredients.

| Parts by weight | |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinylpyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric Coated Tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

d) Suppositories

In the preparation of suppositories, for example, 100 parts by weight of active compound can be incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with another therapeutic agent that is known to treat a disease or condition described herein. For example, with one or more additional pharmaceutical agents that inhibit or prevent the production of VEGF or angiopoietins, attenuate intracellular responses to VEGF or angiopoietins, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include, but are not limited to, anti-edemic steroids, NSAIDS, ras inhibitors, anti-TNF agents, anti-IL1 agents, antihistamines, PAF-antagonists, COX-1 inhibitors, COX-2 inhibitors, NO synthase inhibitors, Akt/PTB inhibitors, IGF-1R inhibitors, PKC inhibitors, PI3 kinase inhibitors, calcineurin inhibitors and immunosuppressants. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deleterious effects of a hyperproliferative disorder, angiogenesis, vascular hyperpermeability or edema than the administration of either substance alone. In the treatment of malignant disorders combinations with antiproliferative or cytotoxic chemotherapies or radiation are included in the scope of the present invention.

The present invention also comprises the use of a compound of Formula (I) as a medicament.

A further aspect of the present invention provides the use of a compound of Formula (I) or a salt thereof in the manufacture of a medicament for treating vascular hyperpermeability, angiogenesis-dependent disorders, proliferative diseases and/or disorders of the immune system in mammals, particularly human beings.

The present invention also provides a method of treating vascular hyperpermeability, inappropriate neovascularization, proliferative diseases and/or disorders of the immune system which comprises the administration of a therapeutically effective amount of a compound of Formula (I) to a mammal, particularly a human being, in need thereof.

| | ABBREVIATIONS |
|---|---|
| ACN | Acetonitrile |
| (R)-BINAP | (R)-(+)-2,2'-Bis(diphenylphosphino)-1,1'-binaphthalene |
| (S)-BINAP | (S)-(−)-2,2'-Bis(diphenylphosphino)-1,1'-binaphthalene |
| Racemic-BINAP | (±)-2,2'-Bis(diphenylphosphino)-1,1'-binaphthalene |
| Boc | tert-Butoxycarbonyl |
| BSA | Bovine serum albumin |
| t-BuOH | tert-Butyl alcohol |
| t-BuOK | Potassium tert-butoxide |
| Cbz | Benzyloxycarbonyl |
| DCC | N,N'-Dicyclohexylcarbodiimide |
| DCM | Dichloromethane |
| DIC | N,N'-Diisopropylcarbodiimide |
| DIEA | N,N-Diisopropylethylamine |
| DMA | N,N-Dimethylacetamide |
| DMAP | 4-N,N-Dimethylaminopyridine |
| DME | 1,2-Dimethoxyethane |
| DMEM | Dulbecco's modified eagle medium |
| DMF | N,N-Dimethylformamide |
| DMFDMA | N,N-Dimethylformamide dimethyl acetal |
| DMSO | Dimethyl sulfoxide |
| DPPF | 1,1'-Bis(diphenylphosphino)ferrocene |
| DTT | Dithiothreitol |
| EDCI | 1-(3-Dimethylaminopropyl)-3-ethylcarbodiimide |
| EDTA | Ethylene diamine tetraacetic acid |
| EPO | Erythropoietin |
| equiv | equivalent |
| $Et_3N$ | Triethylamine |
| $Et_2O$ | Diethyl ether |
| EtOAc | Ethyl acetate |
| FBS | Fetal bovine serum |

ABBREVIATIONS

| | |
|---|---|
| h | hour |
| HOAc | Acetic acid |
| HATU | O-(7-Azabenzotriazol-1-yl)-N,N,N',N'-tetramethyluronium hexafluorophosphate |
| HBTU | O-Benzotriazol-1-yl-N,N,N',N'-tetramethyluronium hexafluorophosphate |
| HCl | Hydrochloric acid |
| HEPES | N-2-Hydroxyethylpiperazine-N'-2-ethanesulfonic acid |
| HOAT | 1-Hydroxy-7-azabenzotriazole |
| HOBT | 1-Hydroxybenzotriazole |
| HPLC | High Pressure Liquid Chromatography |
| KOAc | Potassium acetate |
| LC/MS | Liquid chromatography/mass spectrometry |
| LDA | Lithium diisopropylamide |
| M | Molarity |
| MeOH | Methanol |
| min | minute |
| MOPS | 3-(N-morpholino)-2-hydroxypropanesulfonic acid |
| MOPSO | 3-(N-morpholino)-propanesulfonic acid |
| MP-carbonate | Polymer bound tetraalkylammonium carbonate |
| NBS | N-Bromosuccinimide |
| NIS | N-Iodosuccinimide |
| PMB | p-Methoxybenzyl |
| PPh$_3$ | Triphenylphosphine |
| PPTS | Pyridinium p-toluenesulfonate |
| i-PrOH | 2-Propanol |
| R$_t$ | Retention time |
| RP | Reverse Phase |
| SAXL | Acceptor streptavidin labeled allophycocyanin |
| SEM | 2-(Trimethylsilyl)ethoxymethyl |
| Si-DCT | Silica bound dichlorotriazine |
| TBAF | Tetra-n-butylammonium fluoride |
| TBDMS | tert-Butyldimethylsilane |
| TEA | Triethylamine |
| TFA | Trifluoroacetic acid |
| TFFH | Fluoro-N,N,N',N'-tetramethylformamidinium hexafluorophosphate |
| THF | Tetrahydrofuran |
| TLC | Thin layer chromatography |
| TMS | Trimethylsilyl |
| XANTPHOS | 9,9-Dimethyl-4,5-bis(diphenylphosphino)xanthene |

Assays

In Vitro Jak1 Kinase Activity Measured by Homogenous Time-Resolved Fluorescence (HTRF)

Purified Jak1 enzyme (aa 845-1142; expressed in SF9 cells as a GST fusion and purified by glutathione affinity chromatography) was mixed with 2 µM peptide substrate (biotin-TYR2, Sequence: Biotin-(Ahx)-AEEEYFFLFA-amide) at varying concentrations of inhibitor in reaction buffer: 50 mM MOPSO pH 6.5, 10 mM MgCl$_2$, 2 mM MnCl$_2$, 2.5 mM DTT, 0.01% BSA, 0.1 mM Na$_3$VO$_4$ and 0.001 mM ATP. After about 60 min incubation at room temperature, the reaction was quenched by addition of EDTA (final concentration: 100 mM) and developed by addition of revelation reagents (final approximate concentrations: 30 mM HEPES pH 7.0, 0.06% BSA, 0.006% Tween-20, 0.24 M KF, 80 ng/mL PT66K (europium labeled anti-phosphotyrosine antibody cat #61T66KLB Cisbio, Bedford, Mass.) and 3.12 ug/mL SAXL (Phycolink streptavidin-allophycocyanin acceptor, cat #PJ52S, Prozyme, San Leandro, Calif.). The developed reaction was incubated in the dark either at about 4° C. for about 14 h or for about 60 min at room temperature, then read via a time-resolved fluorescence detector (Rubystar, BMG) using a 337 nm laser for excitation and emission wavelengths of 620 nm and 665 nm. Within the linear range of the assay, the ratio of observed signal at 620 nm and 665 nm is directly related to phosphorylated product and used to calculate the IC$_{50}$ values.

Other kinase assays were performed using a similar protocol. Additional purified enzymes Tyk2 (aa880-1185 with an N-terminal histidine-tag and C-terminal FLAG tag; purified in-house by immobilized metal ion affinity chromatography), RET (aa711-1072 with an N-terminal histidine-tag; purified by immobilized metal ion affinity chromatography) and KDR (aa792-1354 with an N-terminal histidine-tag; purified in-house by immobilized metal ion affinity and ion-exchange chromatography) were expressed in SF9 cells and Aurora 1/B (aa1-344 with a N-terminal histidine-tag and purified by immobilized metal ion affinity chromatography) was expressed in E. coli. Other enzymes used are available from commercial sources. Enzymes were mixed with biotinylated substrates at varying concentrations of inhibitor in different reaction buffers (see Table 1). After about 60 min incubation at room temperature, the reaction was quenched by addition of EDTA and developed by addition of revelation reagents (final approximate concentrations: 30 mM HEPES pH 7.0, 0.06% BSA, 0.006% Tween-20, 0.24 M KF, varying amounts of donor europium labeled antibodies and SAXL. The developed reactions were incubated in the dark at about 4° C. for about 14 h or for about 60 min at room temperature, then read in a time-resolved fluorescence detector (Rubystar, BMG) as described above.

TABLE 1

Specific conditions (per 40 uL enzyme reaction) for the various enzymes are detailed below:

| Enzyme | Construct | Substrate | Assay Buffer | Enzyme Conc. (ng/well) | Substrate Conc. | ATP Conc. (mM) | DMSO Conc. (%) | Reaction Time (min) | Detection condition |
|---|---|---|---|---|---|---|---|---|---|
| Jak1 | aa845-1142 | Biotin-TYR2 | MOPSO | 5 | 2 µM | 0.001 | 5 | 60 | 8 ng/well PT66K, 0.39 µg/well SAXL |
| Jak2 | Millipore cat# 14-640 | Biotin-TYR1 | MOPSO | 2.5 | 2 µM | 0.001 | 5 | 60 | 8 ng/well PT66K, 0.078 µg/well SAXL |
| Jak3 | Millipore cat# 14-629 | Biotin-TYR2 | MOPSO | 1 | 2 µM | 0.001 | 5 | 60 | 8 ng/well PT66K, 0.078 µg/well SAXL |
| Tyk2 | aa880-1185 | Biotin-TYR1 | MOPSO | 9 | 2 µM | 0.001 | 5 | 60 | 8 ng/well PT66K, 0.078 µg/well SAXL |
| Aurora 1/B | aa1-344 | KinEASE S2 | MOPS | 20 | 0.5 µM | 0.1 | 5 | 60 | 15 ng/well Eu-STK-Ab, 0.34 µg/well SAXL |
| KDR | aa789-1354 | Biotin-TYR2 | HEPES | 10 | 2 µM | 0.1 | 5 | 60 | 8 ng/well PT66K, 0.078 µg/well SAXL |
| JNK1 | Millipore cat# 14-327 | Biotin-ATF2-pep | MOPS | 10 | 1 µM | 0.01 | 5 | 60 | 2.58 ng/well Anti-pATF2-Eu, 0.6 µg/well SAXL |
| JNK2 | Millipore cat# 14-329 | Biotin-ATF2-pep | MOPS | 5 | 0.5 µM | 0.01 | 5 | 60 | 2.58 ng/well Anti-pATF2-Eu, 0.6 µg/well SAXL |
| RET | aa711-1072 | Biotin-poly GluTyr | HEPES | 4 | 10 ng/well | 0.01 | 5 | 60 | 8 ng/well PT66K, 0.078 µg/well SAXL |

TABLE 1-continued

Specific conditions (per 40 uL enzyme reaction) for the various enzymes are detailed below:

| Enzyme | Construct | Substrate | Assay Buffer | Enzyme Conc. (ng/well) | Substrate Conc. | ATP Conc. (mM) | DMSO Conc. (%) | Reaction Time (min) | Detection condition |
|---|---|---|---|---|---|---|---|---|---|
| P70 S6 Kinase | Millipore cat# 14-486 | KinEASE S3 | MOPS | 0.5 | 0.25 μM | 0.01 | 5 | 60 | 15 ng/well Eu-STK-Ab, 0.34 μg/well SAXL |
| PKN2 | Invitrogen cat# PV3879 | KinEASE S3 | MOPS | 0.7 | 0.5 μM | 0.001 | 5 | 60 | 15 ng/well Eu-STK-Ab, 0.34 μg/well SAXL |
| Syk | Millipore cat #14-314 | Biotin-TYR1 | MOPSO | 3.8 | 4 μM | 0.01 | 5 | 60 | 11.3 ng/well PT66K, 0.075 μg/well SAXL |
| CDK2/ Cyclin A | Millipore cat# 14-448 | Biotin-MBP | MOPS | 50 | 2 μM | 0.1 | 5 | 60 | 15 ng/well Anti-pMBP-Eu; 0.34 μg/well SAXL |

Reaction Buffers:
MOPSO buffer contains: 50 mM MOPSO pH 6.5, 10 mM $MgCl_2$, 2 mM $MnCl_2$, 2.5 mM DTT, 0.01% BSA, and 0.1 mM $Na_3VO_4$
HEPES buffer contains: 50 mM HEPES pH 7.1, 2.5 mM DTT, 10 mM $MgCl_2$, 2 mM $MnCl_2$, 0.01% BSA, and 0.1 mM $Na_3VO_4$
MOPS buffer contains: 20 mM MOPS pH 7.2, 10 mM $MgCl_2$, 5 mM EGTA, 5 mM Beta-phosphoglycerol, 1 mM $Na_3VO_4$, 0.01% Triton-X-100 and 1 mM DTT
Substrates:
Biotin-ATF2-peptide sequence: Biotin-(Ahx)-AGAGDQTPTPTRFLKRPR-amide
Biotin-TYR1-peptide sequence: Biotin-(Ahx)-GAEEE-IYAAFFA-COOH
Biotin-TYR2-peptide sequence: Biotin-(Ahx)-AEEEYF-FLFA-amide
Biotin-MBP-peptide sequence: Biotin-(Ahx)-VHFFKNIVT-PRTPPPSQGKGAEGQR-amide
Biotin-polyGluTyr peptide was purchased from Cisbio (cat #61GT0BLA, Bedford, Mass.)
KinEASE S2 and S3 peptides were purchased from Cisbio (cat #62ST0PEB, Bedford, Mass.)
Detection Reagents:
Anti-pATF2-Eu was custom-labeled by Cisbio (Bedford, Mass.)
Anti-pMBP-Eu was custom-labeled by Cisbio (Bedford, Mass.)
PT66K was purchased from Cisbio (cat #61T66KLB, Bedford, Mass.)
SAXL was purchased from Prozyme (cat #PJ25S, San Leandro, Calif.)
Human T-Blasts IL-2 pSTAT5 Cellular Assay
Materials:
Phytohemaglutinin T-blasts were prepared from Leukopacks purchased from Biological Specialty Corporation, Colmar, Pa. 18915, and cryopreserved in 5% DMSO/media prior assay.
For this assay the cells were thawed in assay medium with the following composition: RPMI 1640 medium (Gibco 11875093) with 2 mM L-glutamine (Gibco 25030-081), 10 mM HEPES (Gibco 15630-080), 100 U/mL Pen/Strep (Gibco 15140-122), and 10% heat inactivated FBS (Gibco 10438026). Other materials used in the assay: DMSO (Sigma D2650), 96-well dilution plates (polypropylene) (Corning 3365), 96-well assay plates (white, ½ area, 96 well) (Corning 3642), D-PBS (Gibco 14040133), IL-2 (R&D 202-IL-10 (10 μg)), Alphascreen pSTAT5 kit (Perkin Elmer TGRS5S10K) and Alphascreen protein A kit (Perkin Elmer 6760617M).
Methods:
T-Blasts were thawed and cultured for about 24 h without IL-2 prior to assay. Test compounds or controls are dissolved and serially diluted in 100% DMSO. DMSO stocks are subsequently diluted 1:50 in cell culture media to create the 4× compound stocks (containing 2% DMSO). Using a Corning white 96 well, ½ area plate, cells are plated at $2×10^5/10$ uL/well in 10 uL media followed by addition of 5 μL of 4× test compound in duplicate. Cells are incubated with compound for about 0.5 h at about 37° C. Next, 5 μL of IL-2 stock is added at 20 ng/mL final concentration. IL-2 is stored as a 4 μg/mL stock solution, as specified by the manufacturer, at about −20° C. in aliquots and diluted 1:50 with assay media (to 80 ng/mL) just prior to use. The contents of the wells are mixed by carefully tapping the sides of the plate(s) several times followed by incubation at about 37° C. for about 15 min. The assay is terminated by adding 5 of 5× AlphaScreen lysis buffer and shaking on an orbital shaker for about 10 min at room temperature. Alphascreen acceptor bead mix is reconstituted following Perkin Elmer's protocol. 30 μL/well of reconstituted Alphascreen acceptor bead mix was added, covered with foil then shaken on orbital shaker for about 2 min on high then about 2 h on low. Donor bead mix is reconstituted following Perkin Elmer's AlphaScreen protocol; 12 μL/well are added, covered with foil then shaken for about 2 min on high, and about 2 h on low. Plates are read on an EnVision reader following Perkin Elmer's AlphaScreen protocol instructions.
TF-1 IL-6 pSTAT3 Cellular Assay
Materials:
TF-1 cells (ATCC #CRL-2003). Culture medium: DMEM (Gibco 11960-044) with 2 mM L-glutamine (Gibco 25030-081), 10 mM HEPES (Gibco 15630-080), 100 U/mL Pen/Strep (Gibco 15140-122), 1.5 g/L sodium bicarbonate (Gibco 25080-094), 1 mM sodium pyruvate (Gibco 11360-070), 10% heat inactivated FBS (Gibco 10437-028), and 2 ng/mL GM-CSF (R&D 215-GM-010). Other materials used in this assay: DMSO (Sigma D2650), 96-well dilution plates (polypropylene) (Corning 3365), 96-well assay plates (white, ½ area, 96 well) (Corning 3642), D-PBS (Gibco 14040133), IL-6 (R&D 206-IL/CF-050 (50 ug)), Alphascreen pSTAT3 kit (Perkin Elmer TGRS3S10K) and Alphascreen protein A kit (Perkin Elmer 6760617M)
Methods:
Prior to the assay, cells are cultured for about 18 h in the culture medium without GM-CSF. Test compounds or controls are dissolved and serially diluted in 100% DMSO. DMSO stocks are subsequently diluted 1:50 in cell culture media to create the 4× compound stocks (containing 2% DMSO). Using a Corning white 96 well, ½ area plate, cells are plated at $2×10^7/10$ μL/well in 10 μL media followed by addition of 5 μL of the 4× test compound stock in duplicate. Cells are incubated with compound for about 0.5 h at about 37° C. followed by addition of 5 μL of 400 ng/mL IL-6. IL-6 is stored in 10 μg/mL aliquots using endotoxin free D-PBS (0.1% BSA) at about −20° C. Prior to assay IL-6 is diluted to 400 ng/mL in culture media and applied (5 μL/well) to all wells, except to negative control wells where 5 μL/well of media is added. The contents of the wells are mixed carefully by tapping the side of the plate several times. Plates are incubated at about 37° C. for about 30 min. Cells are lysed by adding 5 μL 5× AlphaScreen cell lysis buffer to all wells, shaken for about 10 min at room temperature then assayed. Alternatively, assay plates may be frozen at about −80° C. and thawed later at room temperature. Using the pSTAT3 Sure-Fire Assay kit (Perkin Elmer #TGRS3S10K) acceptor bead mix is reconstituted following Perkin Elmer's AlphaScreen protocol instructions. 30 μL are added per well then the plate is covered with foil and shaken on an orbital shaker for about 2 min on high, then about 2 h on low at room temperature. Donor bead mix is reconstituted following Perkin Elmer's AlphaScreen protocol instructions. 12 μL are added per well, then covered with foil and shaken on orbital shaker for about 2 min on high, then about 2 h on low at about 37° C. Plates are read on an EnVision reader following Perkin Elmer's AlphaScreen protocol instructions at room temperature.

UT7/EPO pSTAT5 Cellular Assay

Materials:

UT7/EPO cells are passaged with EPO, split twice per week and fresh culture medium is thawed and added at time of split. Culture Medium: DMEM medium (Gibco 11960-044) with 2 mM L-glutamine (Gibco 25030-081), 10 mM HEPES (Gibco 15630-080), 100 U/mL Pen/Strep (Gibco 15140-122), 10% heat inactivated FBS (Gibco 10437-028), EPO (5 U/mL=7.1 μL of a 7 μg/mL stock per mL of medium). Assay media: DMEM, 2 mM L-glutamine, 5% FBS, 10 mM HEPES. Other materials used in the assay: DMSO (Sigma D2650), 96-well dilution plates (polypropylene) (Corning 3365), 96-well assay plates (white, ½ area, 96 well) (Corning 3642), D-PBS (Gibco 14040133), IL-2 (R&D 202-IL-10 (10 μg)), Alphascreen pSTAT5 kit (Perkin Elmer TGRS5S10K) and Alphascreen protein A kit (Perkin Elmer 6760617M).

Methods:

Cells are cultured for about 16 h without EPO prior to running assay. Test compounds or controls are dissolved and serially diluted in 100% DMSO. DMSO stocks are subsequently diluted 1:50 in cell culture media to create the 4× compound stocks (containing 2% DMSO). Using a Corning white 96 well, ½ area plate, cells are plated at $2 \times 10^5/10$ μL/well in 10 μL media followed by addition of 5 μL of 4× test compound stock in duplicate. Cells are incubated with compound for about 0.5 h at about 37° C. After incubation, 5 μL of EPO is added to afford a final concentration of 1 nM EPO. The contents of the wells are mixed by carefully tapping sides of the plate several times followed by incubation at about 37° C. for about 20 min. 5 μL of 5× AlphaScreen lysis buffer are added followed by shaking on an orbital shaker for about 10 min at room temperature. 30 μL/well of acceptor beads are added after reconstitution following Perkin Elmer's AlphaScreen protocol, covered with foil and shaken on an orbital shaker for about 2 min on high, then about 2 h on low. Donor beads are reconstituted following Perkin Elmer's AlphaScreen protocol instructions followed by addition of 12 μL/well, covered with foil and shaken on an orbital shaker for about 2 min on high, about 2 h on low. Plates are read on an EnVision reader following Perkin Elmer's AlphaScreen protocol instructions.

Acute in vivo measurement of Jak inhibition of the compounds is measured using the:

Concanavalin A (Con A)-Induced Cytokine Production in Lewis Rats

The test compound is formulated in an inert vehicle (for example but not limited to 0.5% hydroxypropylmethyl cellulose (Sigma, cat #H3785)/0.02% Tween 80 (Sigma, cat #4780) in water)) at the desired concentration to achieve doses in the range of 0.01-100 mg/kg. Six-week-old male Lewis rats (125 g-150 g) (Charles River Laboratories) are dosed with the compound orally, at time zero (0) min. After about 30 min the rats are injected intravenously (i.v.) with 10 mg/kg Concanavalin A (Con A, AmershamBioscience, cat #17-0450-01) dissolved in PBS (Invitrogen, cat #14190). About 4 h later, the rats are cardiac bled and their plasma is analyzed for levels of IL-2 (ELISA kit: R&D Systems cat #R2000) and IFN-γ (ELISA kit: R&D Systems cat #RIF00).

Effects of the compounds on a chronic arthritis disease models in vivo is measured using the:

Adjuvant Induced Arthritis (AIA) in a Lewis Rat

Female Lewis rats, (6 weeks of age, 125 g-150 g in weight from Charles River Laboratories) are immunized intradermally (i.d.) in the right hind-footpad with 100 μL of a suspension of mineral oil (Sigma, cat #M5905) and *M. tuberculosis*, H37RA (Difco, cat #231141). The inflammation appears in the contra-lateral (left) hind paw seven days after the initial immunization. Seven days post immunization, the compound is formulated in an inert vehicle (for example but not limited to 0.5% hydroxypropylmethyl cellulose (Sigma, cat #H3785)/0.02% Tween 80 (Sigma, cat #4780) in water) and dosed orally once or twice a day for at least 10 days. Baseline paw volume is taken on day 0 using a water displacement pleythsmograph (Vgo Basile North America Inc. PA 19473, Model #7140). Rats are lightly anesthetized with an inhalant anesthetic (isoflurane) and the contra-lateral (left) hind paw is dipped into the plethysmograph and the paw volume is recorded. The rats are scored every other day up to day 17 after immunization. On day 17 after immunization, all rats are exsanguinated by cardiac puncture under isoflurane anesthesia, and the left hind paw is collected to assess the impact on bone erosion using micro-CT scans (SCANCO Medical, Southeastern, Pa., Model # μCT 40) at a voxel size of 18 μm, a threshold of 400, sigma-gauss 0.8, support-gauss 1.0. Bone volume and density is determined for a 360 μm (200 slice) vertical section encompassing the tarsal section of the paw. The 360 μm section is analyzed from the base of the metatarsals to the top of the tibia, with the lower reference point fixed at the tibiotalar junction. Drug exposure is determined in the plasma using LC/MS.

The teachings of all references, including journal articles, patents and published patent applications, are incorporated herein by reference in their entirety.

The following examples are for illustrative purposes and are not to be construed as limiting the scope of the present invention.

Compounds of the invention may be prepared using the synthetic transformations illustrated in Schemes I-II. Starting materials are commercially available or may be prepared by the procedures described herein, by literature procedures, or by procedures that would be well known to one skilled in the art of organic chemistry. Methods for preparing pyrazolo[3, 4-d]pyrimidine compounds of the invention are illustrated in Scheme I. 6-Chloro-1H-pyrazolo[3,4-d]pyrimidine (prepared, for example, according to Preparation #2 or US2005277655) is reacted with an alcohol using Mitsunobu conditions such as those described in General Procedure A or by methods known to one skilled in the art (for example, *Bioorganic & Medicinal Chemistry Letters* 2002, 12(12), 1687-1690 or *Tetrahedron Letters* 2007, 48(17), 3057-3059). In Scheme I, step b, a substituted amine is introduced by reaction with pyrazolo[3,4-d]pyrimidines 2 under Buchwald-Hartwig amination conditions (for example, General Procedure B or *Advanced Synthesis & Catalysis* 2004, 346, 1599-1626) to give pyrazolo[3,4-d]pyrimidines 3. Deprotection of pyrazolo[3,4-d]pyrimidines 3 can be performed using conditions such as those described in Greene, T. W. and Wuts, P. G. M. referenced above or in General Procedure C. For example, a protecting group such as a benzyloxycarbonyl group can be removed from a protected amine to yield the unprotected amine (for example, Example #C.1) and the deprotected compounds may then be reacted further. Further functionalization of the resulting pyrazolopyrimidines can be performed, if desired, using reactions known to one skilled in the art (for example, Larock, R. C. "Comprehensive Organic Transformations: A Guide to Functional Group Preparations, 2$^{nd}$ edition", 1999, Wiley-VCH). For example, formation of amides, ureas, sulfonamides, aryl amines, or heteroaryl amines can be achieved by reaction of pyrazolopyrimidines containing a primary or secondary amine (for example, General Procedure D or Example #D.1).

Scheme I:

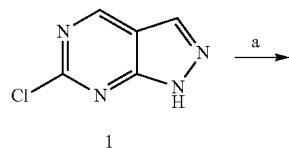

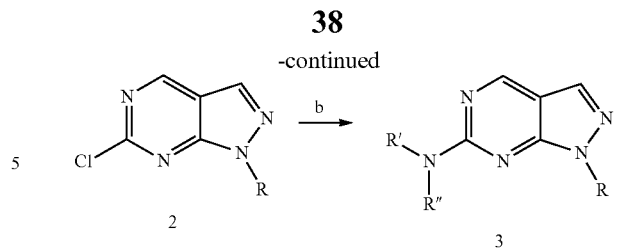

Alternate methods for preparing pyrazolo[3,4-d]pyrimidine compounds of the invention are illustrated in Scheme II. 1H-Pyrazolo[3,4-d]pyrimidine 5 can be prepared (Scheme II, step a) from commercially available 4-chloro-1H-pyrazolo[3,4-d]pyrimidin-6-amine 4 according to conditions such as those described in Preparation #3 or *Chemical & Pharmaceutical Bulletin* 1987, 35(12), 4803-4812. 1H-Pyrazolo[3,4-d]pyrimidines 5 can then be reacted with a substituted aryl halide or heteroaryl halide under Buchwald-Hartwig amination conditions (for example, General Procedure B or *Advanced Synthesis & Catalysis* 2004, 346, 1599-1626) to give pyrazolo[3,4-d]pyrimidines 6. Alternatively, 1H-pyrazolo[3,4-d]pyrimidines 5 can be reacted with an alcohol using conditions such as those described in General Procedure A or by methods known to one skilled in the art (for example, *Bioorganic & Medicinal Chemistry Letters* 2002, 12(12), 1687-1690 or *Tetrahedron Letters* 2007, 48(17), 3057-3059) to give pyrazolo[3,4-d]pyrimidines 7. Deprotection of pyrazolopyrimidines 6 or 7 can be performed using conditions such as those described in Greene, T. W. and Wuts, P. G. M. referenced above or in General Procedure C. For example, a protecting group such as a benzyloxycarbonyl group can be removed from a protected amine to yield the unprotected amine (for example, Example #C.1.1.) and the deprotected compounds may then be reacted further as described above. Further functionalization of the resulting pyrazolopyrimidines can be performed, if desired, using reactions known to one skilled in the art (for example, Larock, R. C. referenced above). For example, formation of amides, ureas, sulfonamides, aryl amines, or heteroaryl amines can be achieved by reaction of pyrazolopyrimidines containing a primary or secondary amine (for example, General Procedure D or Example #D.1.1.).

Scheme II:

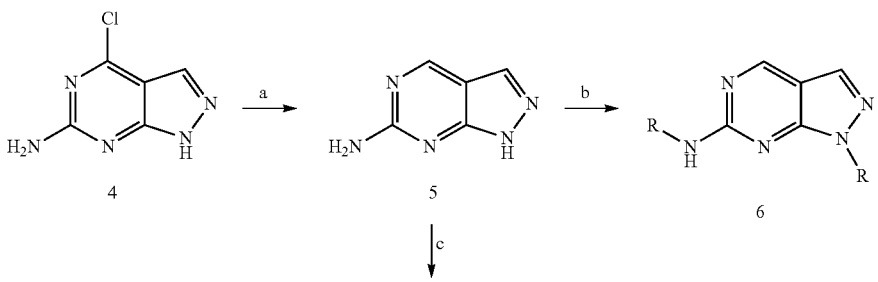

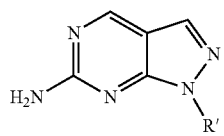

GENERAL PROCEDURES AND EXAMPLES

The general synthetic schemes that were utilized to construct the majority of compounds disclosed in this application are described below in Schemes 1-4. These schemes are provided for illustrative purposes only and are not to be construed as limiting the scope of the invention.

Scheme 1. Mitsunobu coupling of pyrazolo[3,4-d]pyrimidines (General Procedure A)

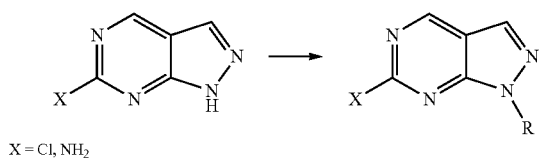

X = Cl, NH$_2$

Scheme 2. Pd-catalyzed amination reaction (General Procedure B)

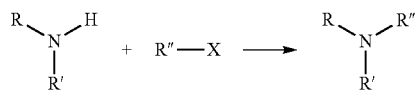

Scheme 3. Acidic cleavage of a Boc-protected amine (General Procedure C)

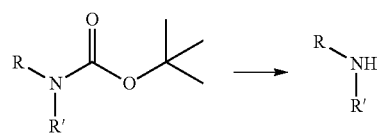

Scheme 4. Formation of an amide from an activated acid and an amide (General Procedure D)

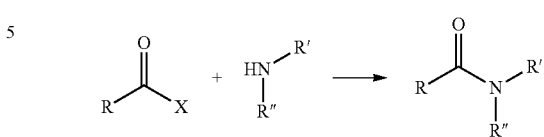

List of General Procedures

General Procedure A: Mitsunobu coupling of pyrazolo[3,4-d]pyrimidines
General Procedure B: Pd-catalyzed amination reaction
General Procedure C: Acidic cleavage of a Boc-protected amine
General Procedure D: Formation of an amide from an activated acid and an amine The following examples are ordered according to the final general procedure used in their preparation. The synthetic routes to any novel intermediates are detailed by sequentially listing the general procedure (letter codes) in parentheses after their name with additional reactants or reagents as appropriate. A worked example of this protocol is given below using Example #C.1.2 as a non-limiting illustration. Example #C.1.2 is 5-(1-(((1R,4R)-4-(aminomethyl)cyclohexyl)methyl)-1H-pyrazolo[3,4-d]pyrimidin-6-ylamino)-2-methylbenzenesulfonamide, which was prepared from tert-butyl ((1R,4R)-4-((6-(4-methyl-3-sulfamoylphenylamino)-1H-pyrazolo[3,4-d]pyrimidin-1-yl)methyl)cyclohexyl)methylcarbamate using General Procedure C as represented in Scheme A.

Scheme A

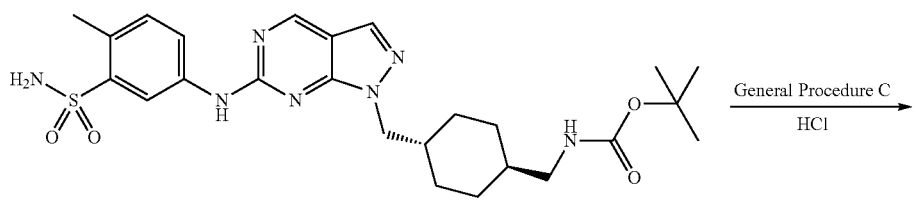

Precursor to Example #C.1.2

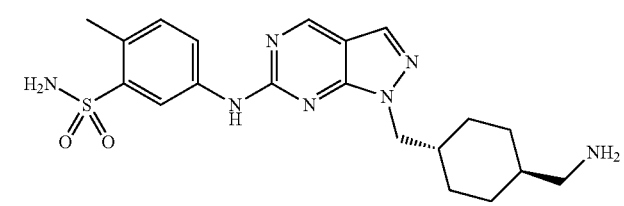

Example #C.1.2

The precursor to Example #C.1.2, tert-butyl ((1R,4R)-4-((6-(4-methyl-3-sulfamoylphenylamino)-1H-pyrazolo[3,4-d]pyrimidin-1-yl)methyl)cyclohexyl)methylcarbamate, was prepared as shown in Scheme B. 6-Chloro-1H-pyrazolo[3,4-d]pyrimidine (Preparation #2) and tert-butyl (trans-4-hydroxymethylcyclohexylmethyl)carbamate are reacted following the conditions given in General Procedure A to give tert-butyl ((1R,4R)-4-((6-chloro-1H-pyrazolo[3,4-d]pyrimidin-1-yl)methyl)cyclohexyl)methylcarbamate. This heteroaryl halide is reacted with 5-amino-2-methylbenzenesulfonamide using the conditions given in General Procedure B to afford tert-butyl ((1R,4R)-4-((6-(4-methyl-3-sulfamoylphenylamino)-1H-pyrazolo[3,4-d]pyrimidin-1-yl)methyl)cyclohexyl)methylcarbamate, the precursor to Example #C.1.2. The reaction sequence detailed above is translated in the preparations and examples section to "using A from Preparation #2 and tert-butyl (trans-4-hydroxymethylcyclohexylmethyl)carbamate [AMRI], B from 5-amino-2-methylbenzenesulfonamide [Waterstone.

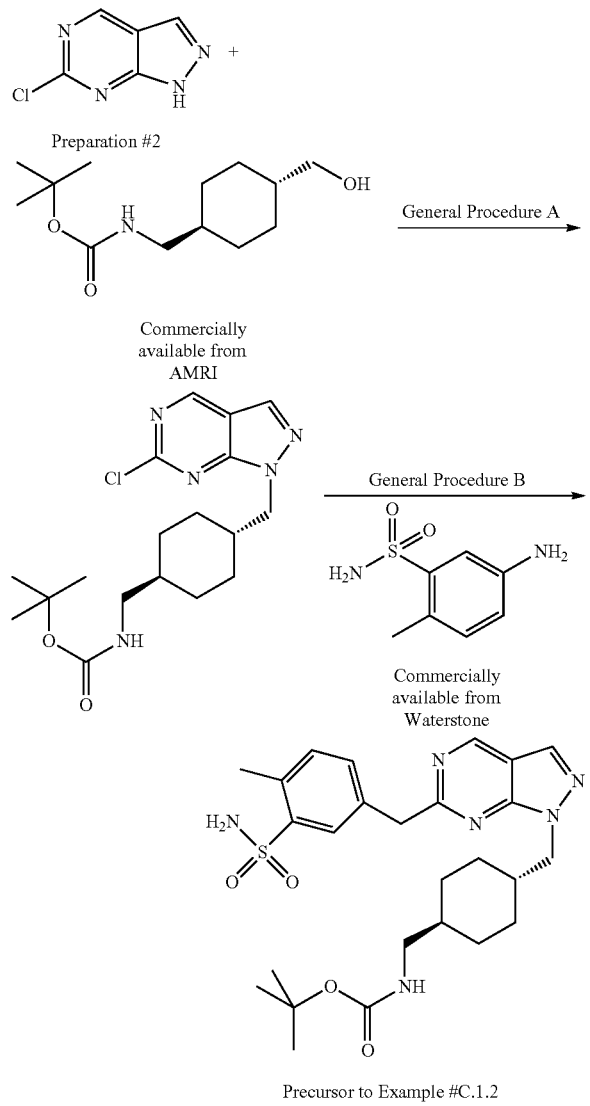

Scheme B

Preparation #2

Commercially available from AMRI

General Procedure A

General Procedure B

Commercially available from Waterstone

Precursor to Example #C.1.2

Analytical Methods

Analytical data is included within the procedures below, in the illustrations of the general procedures, or in the tables of examples. Unless otherwise stated, all $^1$H NMR data were collected on a Varian Mercury Plus 400 MHz or a Varian Inova 600 MHz instrument and chemical shifts are quoted in parts per million (ppm). LC/MS and HPLC data is referenced to the table of LC/MS and HPLC conditions using the lower case method letter provided in Table 2.

TABLE 2

LC/MS and HPLC methods

| Method | Conditions |
|---|---|
| a | LC/MS: The gradient was 5-60% B in 1.5 min then 60-95% B to 2.5 min with a hold at 95% B for 1.2 min (1.3 mL/min flow rate). Mobile phase A was 10 mM ammonium acetate, mobile phase B was HPLC grade ACN. The column used for the chromatography is a 4.6 × 50 mm MAC-MOD Halo C8 column (2.7 μm particles). Detection methods are diode array (DAD) and evaporative light scattering (ELSD) detection as well as positive/negative electrospray ionization |
| b | HPLC: The column used for the chromatography was a 21.2 × 250 mm Hypersil C18 HS column (8 μm particles). The gradient was 15-80% B over 25 min (21 mL/min flow rate). Mobile phase A was 0.05N aqueous ammonium acetate buffer (pH 4.5) and mobile phase B was HPLC grade ACN. Detection method is UV, λ = 254 nm |
| c | HPLC: The column used for the chromatography is a 4.6 × 30 mm Vydac Genesis C8 column (4 μm particles). The gradient was 5-60% B in 1.5 min then 60-95% B to 2.5 min with a hold at 95% B for 1.2 min (1.3 mL/min flow rate). Mobile phase A was 10 mM ammonium acetate, mobile phase B was HPLC grade ACN. Detection methods are diode array (DAD) and evaporative light scattering (ELSD) detection as well as positive and negative electrospray ionization. |

Preparations and Examples

The general synthetic methods used in each General Procedure follow and include an illustration of a compound that was synthesized using the designated General Procedure. None of the specific conditions and reagents noted herein are to be construed as limiting the scope of the invention and are provided for illustrative purposes only. The described compounds can be isolated as either the free base or a salt form of any stoichiometry (i.e. 1, 1.5, 2, 3 . . . ) depending on the method of purification. For example, a compound purified by a preparatory HPLC method that contains ammonium acetate may be isolated as a mono-, di- or tri-acetate salt. Alternatively a compound purified by flash chromatography on silica gel may be isolated as a free base. These examples are not meant to be limiting in the form of the material, the type of salt or the stoichiometry of the salt. The final form, free base or salt form, of the material was determined through standard characterization techniques (i.e. NMR integration, elemental analysis). All starting materials are commercially available from Sigma-Aldrich (including Fluka and Discovery CPR) unless otherwise noted after the chemical name. Reagent/reactant names given are as named on the commercial bottle or as generated by IUPAC conventions or by CambridgeSoft® ChemDraw Ultra 9.0.7.

Preparation #1:
2,4-Dichloropyrimidine-5-carbaldehyde

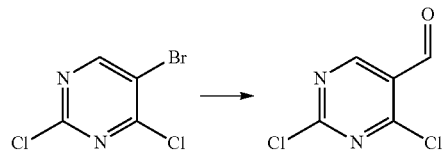 [SMILES: Clc1ncc(Br)c(Cl)n1 ; O=Cc1cnc(Cl)nc1Cl]

A solution of isopropyl magnesium chloride lithium chloride complex in THF (2M, 184 mL, 368 mmol) was added drop-wise over about 30 min to a 2 L round-bottomed flask charged with a solution of 5-bromo-2,4-dichloropyrimidine (49.6 g, 218 mmol) in THF (1000 mL) at about −78° C. The reaction was allowed to stir at about −78° C. for about 30 min. Morpholine-4-carbaldehyde (75.0 g, 653 mmol) was then added drop-wise at about −78° C. over about 30 min. The reaction was allowed to stir for about 30 min at about −78° C. then allowed to warm to about −35° C. and stirred for about 30 min. Aqueous HCl (1N, 250 mL) and Et$_2$O (500 mL) were added and the reaction mixture was allowed to warm to ambient temperature. The organic layer was separated and the aqueous layer was further extracted with Et$_2$O (200 mL). The combined organic layers were dried over anhydrous MgSO$_4$, filtered through a silica gel pad on a fritted funnel, and concentrated under reduced pressure. The crude material was purified by silica gel chromatography using DCM (100%) as the eluent to provide 2,4-dichloropyrimidine-5-carbaldehyde (27.3 g, 71%) as a light yellow solid. $^1$H NMR (400 MHz, CDCl$_3$) δ 10.34 (s, 1H), 9.30 (s, 1H).

Preparation #2:
6-Chloro-1H-pyrazolo[3,4-d]pyrimidine

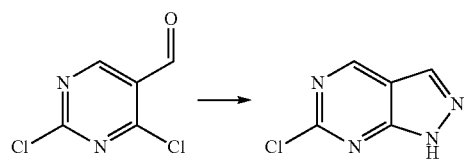 [SMILES: O=Cc1cnc(Cl)nc1Cl ; Clc1ncc2cn[nH]c2n1]

A solution of 2,4-dichloropyrimidine-5-carbaldehyde (7.75 g, 43.8 mmol, Preparation #1) in THF (100 mL) was added to a 500 mL round-bottomed flask charged with anhydrous hydrazine (3.0 mL, 96 mmol) in THF (250 mL). The reaction mixture was allowed to stir at ambient temperature for about 1 h after which the reaction mixture was concentrated under reduced pressure. The crude product was suspended in DCM (100 mL) and filtered through a silica gel pad. The silica gel pad was washed with additional DCM (2×20 mL) and the combined organic layers were concentrated under reduced pressure. The crude material was purified by silica gel chromatography eluting with 30% EtOAc in heptane to provide 6-chloro-1H-pyrazolo[3,4-d]pyrimidine (2.3 g, 34%) as a white solid. LC/MS (Table 2, Method a) R$_t$=1.29 min; MS m/z: 155 (M+H)$^+$.

Preparation #3: 1H-Pyrazolo[3,4-d]pyrimidin-6-yl amine

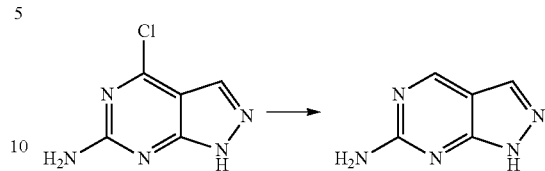

A mixture containing 4-chloro-1H-pyrazolo[3,4-d]pyrimidin-6-yl amine (0.6 g, 3.54 mmol, Chembridge), 10% palladium on carbon (0.15 g), ammonium formate (1.24 g, 19.6 mmol) and methanol (20 mL) was heated at reflux for about 4 h. The reaction mixture was cooled to ambient temperature and filtered through Celite®, which was subsequently washed with additional MeOH (2×20 mL). The combined filtrates were evaporated under reduced pressure to yield a white solid. The solid was suspended in water (50 mL), filtered, and dried to afford 1H-pyrazolo[3,4-d]pyrimidin-6-yl amine (0.15 g, 31%) as a white solid. LC/MS (Table 2, Method c) R$_t$=2.12 min; MS m/z: 136 (M+H)$^+$.

General Procedure A: Mitsunobu Coupling of pyrazolo[3,4-d]pyrimidines

To a solution of a pyrazolo[3,4-d]pyrimidine (preferably 1 equiv) in an organic solvent (for example, THF, 1,4-dioxane or DME, preferably THF) is added an alcohol (1-5 equiv, preferably 1.5 equiv), Ph$_3$P (1-3 equiv, preferably 1.2 equiv) followed by an azodicarboxylate (for example diisopropyl azodicarboxylate or diethyl azodicarboxylate, preferably diethyl azodicarboxylate; 1-3 equiv, preferably 1.5 equiv) at ambient temperature. After about 1-48 h (preferably about 16 h), the reaction is concentrated under reduced pressure. The crude product is purified by crystallization or trituration from an appropriate solvent or solvents, or by chromatography to give the target compound.

Illustration of General Procedure A

Preparation #A.1.1: tert-Butyl (trans-4-((6-chloro-1H-pyrazolo[3,4-d]pyrimidin-1-yl)methyl)cyclohexyl)methylcarbamate

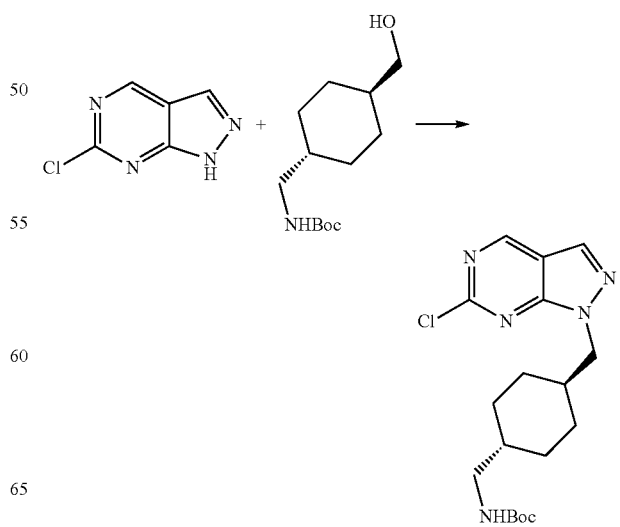

Diethyl azodicarboxylate (1.33 mL, 3.35 mmol) was added drop-wise over about 2 min to a 250 mL round-bottomed flask charged with 6-chloro-1H-pyrazolo[3,4-d]pyrimidine (0.345 g, 2.23 mmol, Preparation #2), tert-butyl (trans-4-hydroxymethyl)cyclohexyl)methylcarbamate (0.815 g, 3.35 mmol, AMRI), and triphenylphosphine (0.703 g, 2.68 mmol) in THF (20 mL). The reaction was allowed to stir for about 16 h at ambient temperature then concentrated under reduced pressure and the crude product was purified by silica gel chromatography eluting with 35% EtOAc in heptane to provide tert-butyl (trans-4-((6-chloro-1H-pyrazolo[3,4-d]pyrimidin-1-yl)methyl)cyclohexyl)methylcarbamate (0.835 g, 98%) as a white solid. LC/MS (Table 2, Method a) $R_t$=2.59 min; MS m/z: 381 (M+H)$^+$.

TABLE A.1

Examples prepared from 1H-pyrazolo[3,4-d]pyrimidin-6-yl amine (Preparation #3) using General Procedure A

| Alcohol | Product | Example # | $R_t$ min (Table 2, Method) | m/z ESI+ (M + H)$^+$ |
|---|---|---|---|---|
| tert-butyl (1S,4S)-4-(hydroxymethyl)cyclohexylcarbamate [AMRI] | (structure) | A.1.2 | 1.84 (a) | 347 |

TABLE A.2

Examples prepared from 6-chloro-1H-pyrazolo[3,4-d]pyrimidin-6-yl amine (Preparation #2) using General Procedure A

| Alcohol | Product | Ex# | NMR |
|---|---|---|---|
| tert-butyl ((1R,4R)-4-(hydroxymethyl)cyclohexyl)methylcarbamate [AMRI] | (structure) | A.2.1 | $^1$H NMR (300 MHz, DMSO-D$_6$) δ ppm 1.01-1.12 (m, 2 H) 1.36 (s, 9 H) 1.45-1.55 (m, J = 6.8 Hz, 2 H) 1.69-1.90 (m, 4 H) 3.06-3.22 (m, 2 H) 4.24 (d, J = 7.1 Hz, 2 H) 6.64 (d, J = 8.14 Hz, 1 H) 8.96 (s, 2 H) |
| tert-butyl ((1R,4R)-4-(hydroxymethyl)cyclohexyl)methylcarbamate [AMRI] | (structure) | A.2.2 | $^1$H NMR (300 MHz, DMSO-D$_6$) δ ppm 5.69 (s, 2 H) 7.37 (dd, J = 7.9, 4.8 Hz, 1 H) 7.49-7.72 (m, 2 H) 8.47-8.53 (m, 1 H) 8.57 (d, J = 2.0 Hz, 1 H) 9.30 (s, 1 H) |

General Procedure B: Pd-Catalyzed Amination Reaction

To a solution of a halide (1-3 equivalents, preferably 1 equiv) in an organic solvent (for example, DMF, THF or 1,4-dioxane, preferably 1,4-dioxane) is added a base (for example sodium tert-butoxide, sodium methoxide, potassium tert-butoxide, preferably sodium tert-butoxide; 1-10 equiv, preferably 2.5-3 equiv) and an amine (1-5 equiv, preferably 1.3-1.5 equiv). To this solution is added a solution of a palladium catalyst (such as Pd$_2$(dibenzylideneacetone)$_3$ or palladium acetate, preferably Pd$_2$(dibenzylideneacetone)$_3$; 0.01-0.5 equiv, preferably 0.1 equiv) and a phosphine ligand (such as 2-dicyclohexylphosphino-2',4',6'-triisopropylbiphenyl or 2-di-tert-butylphosphino-2',4',6'-triisopropylbiphenyl, preferably 2-di-tert-butylphosphino-2',4',6'-triisopropylbiphenyl; 0.01-0.5 equiv, preferably 0.2-0.4 equiv) in an organic solvent (for example, DMF, THF or 1,4-dioxane, preferably 1,4-dioxane). The catalyst is pre-activated by heating at about 60-120° C. (preferably about 80° C.) for about 1-30 min (preferably about 2 min). After about 1-48 h (preferably about 16 h), the reaction mixture is allowed to cool to ambient temperature then water and an organic solvent (such as EtOAc or DCM, preferably EtOAc) are added. The organic layer is separated. The aqueous layer is optionally extracted with additional organic solvents. The organic layers are dried over anhydrous Na$_2$SO$_4$ or MgSO$_4$, filtered, and concentrated under reduced pressure. The crude product is purified by crystallization or trituration from an appropriate solvent or solvents, or by chromatography to give the target compound.

Illustration of General Procedure B

Example #B.1.1

Tert-Butyl-cis-4-((6-(4-methyl-3-sulfamoylphenylamino)-1H-pyrazolo[3,4-d]pyrimidin-1-yl)methyl)cyclohexylcarbamate

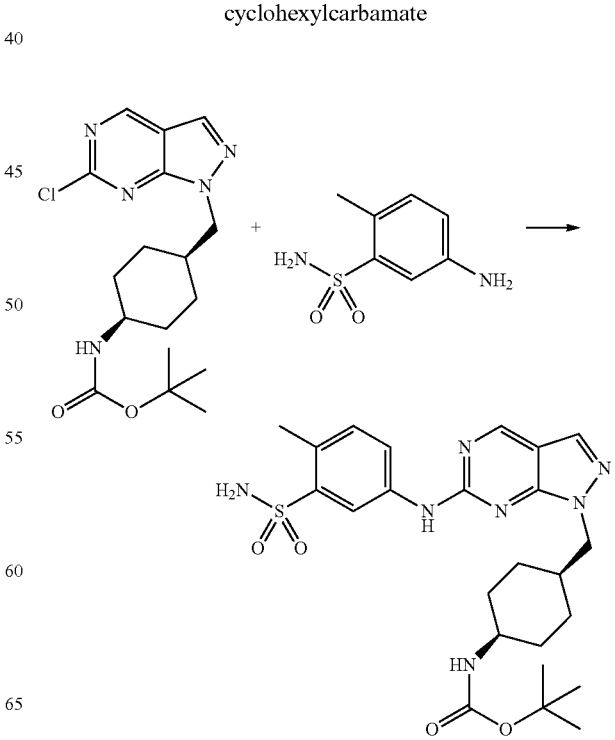

A solution of tert-butyl-cis-4-((6-chloro-1H-pyrazolo[3,4-d]pyrimidin-1-yl)methyl)cyclohexylcarbamate (1.66 g, 4.53 mmol, prepared using A from Preparation #2 and tert-butyl-cis-(4-hydroxymethyl)cyclohexylcarbamate [AMRI]), 5-amino-2-methylbenzenesulfonamide (1.10 g, 5.89 mmol, Waterstone), and sodium tert-butoxide (1.306 g, 13.59 mmol) in 1,4-dioxane (15 mL) was stirred at ambient temperature for about 30 min. In a separate 10 mL nitrogen purged vial charged with Pd$_2$(dibenzylideneacetone)$_3$ (0.415 g, 0.453 mmol) and 2-di-tert-butylphosphino-2',4',6'-triisopropylbiphenyl (0.789 g, 1.86 mmol) was added 1,4-dioxane (2 mL) followed by heating to about 80° C. for about 2 min. The mixture was subsequently cooled to ambient temperature. The catalyst solution was added to the reaction mixture at ambient temperature and the reaction mixture was heated to about 80° C. for about 16 h. The reaction mixture was cooled to ambient temperature then water (100 mL) and EtOAc (50 mL) were added and the organic layer was separated. The aqueous layer was further extracted with EtOAc (2×50 mL) and the combined organic extracts were dried over anhydrous MgSO$_4$, filtered through a silica gel pad, and concentrated under reduced pressure. The crude residue was purified by silica gel chromatography eluting with 50% EtOAc in heptane to provide tert-butyl-cis-4-((6-(4-methyl-3-sulfamoylphenylamino)-1H-pyrazolo[3,4-d]pyrimidin-1-yl)methyl)cyclohexylcarbamate (0.58 g, 25%) as a light yellow solid. LC/MS (Table 2, Method a) R$_t$=1.38 min; MS m/z: 516 (M+H)$^+$.

TABLE B.1

Examples prepared using General Procedure B

| Amine | Halide | Product | Ex. # | R$_t$ min (method) | m/z ESI |
|---|---|---|---|---|---|
| 4-(4-methylpiperazin-1-yl)aniline [SynChem] | tert-butyl (trans-4-((6-chloro-1H-pyrazolo[3,4-d]pyrimidin-1-yl)methyl)cyclohexyl)methylcarbamate (Preparation #A.1) | | B.1.2 | 1.85 (a) | 535 (M + H)$^+$ |
| 1H-pyrazolo[3,4-d]pyrimidin-6-yl amine (Preparation #3) | 3-bromo-N,N-dimethylbenzenesulfonamide [CombiBlocks] | | B.1.3 | 2.65 (c) | 500 (M − H)$^−$ |
| 3-aminobenzenesulfonamide [Alfa Aesar] | tert-butyl (trans-4-((6-chloro-1H-pyrazolo[3,4-d]pyrimidin-1-yl)methyl)cyclohexyl)methylcarbamate (Preparation #A.1) | | B.1.4 | 2.21 (a) | 514 (M − H)$^−$ |
| 4-(4-methylpiperazin-1-yl)aniline [SynChem] | tert-butyl (1R,4R)-4-((6-chloro-1H-pyrazolo[3,4-d]pyrimidin-1-yl)methyl)cyclohexylcarbamate (prepared using A from Preparation #2 and tert-butyl-trans-(1R,4R)-4-(hydroxymethyl)cyclohexylcarbamate [AMRI]) | | B.1.5 | 1.80 (a) | 521 (M + H)$^+$ |

TABLE B.1-continued

Examples prepared using General Procedure B

| Amine | Halide | Product | Ex. # | R$_t$ min (method) | m/z ESI |
|---|---|---|---|---|---|
| 5-amino-2-methylbenzene-sulfonamide [Waterstone] | tert-butyl 4-(6-chloro-1H-pyrazolo[3,4-d]pyrimidin-1-yl)piperidine-1-carboxylate (prepared using A from Preparation #2 and tert-butyl 4-hydroxypiperidine-1-carboxylate) | | B.1.6 | 2.14 (a) | 488 (M + H)+ |
| 4-(4-methylpiper-azin-1-yl)aniline [SynChem] | tert-butyl 4-(6-chloro-1H-pyrazolo[3,4-d]pyrimidin-1-yl)piperidine-1-carboxylate (prepared using A from Preparation #2 and tert-butyl 4-hydroxypiperidine-1-carboxylate) | | B.1.7 | 1.79 (a) | 493 (M + H)+ |
| 5-amino-2-methylbenzene-sulfonamide [Waterstone] | tert-butyl (1S,4S)-4-(6-chloro-1H-pyrazolo[3,4-d]pyrimidin-1-yl)cyclohexylcarba-mate (prepared using A from Preparation #2 and tert-butyl (1S,4S)-4-hydroxycyclohexyl-carbamate) | | B.1.8 | 2.17 (a) | 502 (M + H) |
| 4-amino-N-(3-chlorophenyl)benzenesulfon-amide | 6-chloro-1 (pyridine-3-ylmethyl)-1H-pyrazolo[3,4-d]pyrimidine (Ex. #A.2.2) | | B.1.9 | 1.39 (b) | 492 (M + H)+ |

TABLE B.1-continued

Examples prepared using General Procedure B

| Amine | Halide | Product | Ex. # | R$_t$ min (method) | m/z ESI |
|---|---|---|---|---|---|
| 1-methyl-1H-pyrazol-4-amine | 6-chloro-1-(pyridine-3ylmethyl)-1H-pyrazolo[3,4-d]pyrimidine (Ex. #A.2.2) | | B.1.10 | 0.32 (b) | 307 (M + H)$^+$ |
| 5-amino-2-methylbenzene-sufonamide | 6-chloro-2-phenyl-2H-pyrazolo[3,4-d]pyrimidine | | B.1.11 | 1.44 (b) | 381 (M + H)$^+$ |
| 5-amino-2-methylbenzene-sufonamide | 6-chloro-1-phenyl-1H-pyrazolo[3,4-d]pyrimidine | | B.1.12 | 1.44 (b) | 381 (M + H)$^+$ |

TABLE B.2

Examples prepared using General Procedure B

| Amine | Halide | Product | Ex. # | NMR | R$_t$ or m/z ESI+ (M + H)$^+$ |
|---|---|---|---|---|---|
| 1-methyl-1H-pyrazol-4-amine (Matrix) | tert-butyl ((1R,4R)-4-((6-chloro-1H-pyrazolo[3,4-d]pyrimidin-1-yl)methyl)cyclohexyl)methylcarbamate (Ex #A.2.1) | | B.2.1 | $^1$H NMR (300 MHz, DMSO-D$_6$) δ ppm 0.92-1.20 (m, 4 H) 1.35 (s, 9 H) 1.56 (s, 2 H) 1.67-1.94 (m, 3 H) 3.16 (s, 1 H) 3.81-3.90 (m, 3 H) 4.15 (d, J = 6.7 Hz, 2 H) 6.65 (d, J = 7.5 Hz, 1 H) 7.45-7.77 (m, 2 H) 7.86-8.14 (m, 2 H) 8.89 (s, 1 H) 9.78 (s, 1 H) | 1.49 (a) |

TABLE B.2-continued

Examples prepared using General Procedure B

| Amine | Halide | Product | Ex. # | NMR | $R_t$ or m/z ESI+ $(M + H)^+$ |
|---|---|---|---|---|---|
| 2-(4-amino-1H-pyrazol-1-yl)ethanol. | tert-butyl ((1R,4R)-4-((6-chloro-1H-pyrazolo[3,4-d]pyrimidin-1-yl)methyl)cyclohexyl)methylcarbamate (Ex #A.2.1) | | B.2.2 | $^1$H NMR (300 MHz, DMSO-D$_6$) δ ppm 0.91-1.19 (m, 4 H) 1.24-1.38 (m, 9 H) 1.56 (s, 2 H) 1.75 (s, 4 H) 3.16 (s, 2 H) 3.75 (q, J = 5.4 Hz, 2 H) 4.13 (t, J = 5.6 Hz, 2 H) 6.63 (d, J = 7.8 Hz, 1 H) 7.62 (s, 1 H) 8.00 (s, 1 H) 8.08 (s, 1 H) 8.89 (s, 1 H) 9.77 (s, 1 H) | 457 |
| Pyridine-3-ylmethanol (Aldrich) | 6-Chloro-1-(pyridin-3-ylmethyl)-1H-pyrazolo[3,4-d]pyrimidine (Ex. #A.2.2) | | B.2.3 | $^1$H NMR (300 MHz, DMSO-D$_6$) δ ppm 3.84 (s, 3 H) 5.69 (s, 2 H) 7.53-7.65 (m, 2 H) 7.94 (d, J = 7.8 Hz, 1 H) 8.04 (s, 1 H) 8.63 (dd, J = 5.1, 1.36 Hz, 1 H) 8.73 (s, 1 H) 8.93 (s, 1 H) 9.88 (s, 1 H) | 307 $(M + H)^+$ |
| 5-amino-2-methyl-benzenesulfonamide | 6-Chloro-1-(pyridine-3-ylmethyl)-1-H-pyrazolo[3,4-d]pyrimidine (Ex. #A.2.2) | | B.2.4 | $^1$H NMR (300 MHz, DMSO δ 10.20 (s, 1H), 9.02 (s, 1H), 8.86 (d, J = 2.4 Hz, 1H), 8.65 (d, J = 2.2 Hz, 1H), 8.49 (dd, J = 4.8, 1.6 Hz, 1H), 8.14 (s, 1H), 7.84-7.71 (m, 2H), 7.40-7.27 (m, 5H), 5.60 (bs, 2H), 2.55 (d, J = 2.1 Hz, 1H), 1.90 (s, 1H). | 396 |

TABLE B.2-continued

Examples prepared using General Procedure B

| Amine | Halide | Product | Ex. # | NMR | $R_f$ or m/z ESI+ $(M + H)^+$ |
|---|---|---|---|---|---|
| 4-(4-methyl-piperazin-1-yl)aniline | 6-Chloro-1-(pyridine-3-ylmethyl)-1H-pyrazolo[3,4-d]pyrimidine (Ex. #A.2.2) | | B.2.5 | $^1$H NMR (300 MHz, DMSO) δ 9.72 (d, J = 8.9 Hz, 1H), 8.93 (s, 1H), 8.61-8.47 (m, 2H), 8.07 (s, 1H), 7.72-7.63 (m, 3H), 7.41-7.33 (m, 1H), 6.95-6.88 (m, 2H), 5.53 (bs, 2H), 3.11-3.04 (m, 4H), 2.52-2.49 (m, 4H), 2.22 (s, 3H). | 401 |
| 4-(4-Amino-phenyl)thiomorpholine 1,1-dioxide | 6-Chloro-1-(puridin-3-ylmethyl)-1H-pyrazolo[3,4-d]pyrimidine (Ex. #A.2.2) | | B.2.6 | $^1$H NMR (300 MHz, DMSO) δ 9.78 (s, 1H), 8.95 (s, 1H), 8.61-8.47 (m, 2H), 8.08 (s, 1H), 7.77-7.63 (m, 3H), 7.37 (dd, J = 7.9, 4.8 Hz, 1H), 7.11-6.99 (m, 2H), 5.54 (bs, 2H), 3.74-3.67 (m, 4H), 3.22-3.07 (m, 4H). | 436 |

General Procedure C: Acidic Cleavage of a Boc-Protected Amine

To a solution of a Boc-protected amine (preferably 1 equiv) in an organic solvent (for example, THF, 1,4-dioxane, MeOH or DCM, preferably MeOH, 1,4-dioxane or DCM) is added an acid (such as 6N aqueous HCl or TFA, preferably TFA; 1-100 equiv, preferably about 10 equiv). The mixture is stirred at about 0-80° C. (preferably ambient temperature). After about 1-24 h (preferably about 2 h), the reaction mixture is concentrated under reduced pressure and the residue is optionally partitioned between a basic aqueous solution (such as aqueous $Na_2CO_3$, $NaHCO_3$ or NaOH, preferably aqueous NaOH) and an organic solvent (EtOAc or DCM, preferably EtOAc). The organic extract is dried over anhydrous $Na_2SO_4$ or $MgSO_4$, filtered and concentrated under reduced pressure. The crude product is purified by crystallization or trituration from an appropriate solvent or solvents, or by chromatography to give the target compound.

Illustration of General Procedure C

Example #C.1.1

5-(1-((cis-4-Aminocyclohexyl)methyl)-1H-pyrazolo[3,4-d]pyrimidin-6-ylamino)-2-methylbenzenesulfonamide

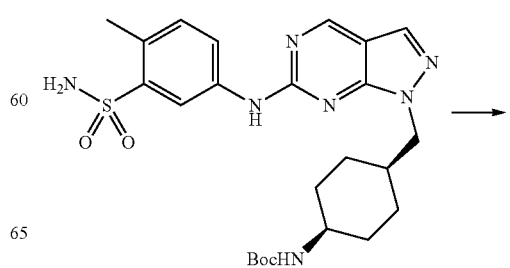

-continued

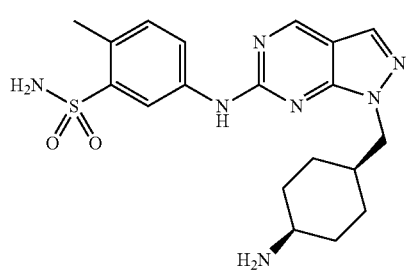

TFA (1.0 mL, 13 mmol) was added drop-wise over about 1 min to a 100 mL round-bottomed flask containing a solution of tert-butyl-cis-4-((6-(4-methyl-3-sulfamoylphenylamino)-1H-pyrazolo[3,4-d]pyrimidin-1-yl)methyl)cyclohexylcarbamate (0.55 g, 1.1 mmol, Example #B.1.1) in DCM (5 mL) at ambient temperature. The reaction mixture was allowed to stir for about 2 h then concentrated under reduced pressure. The crude product was purified by RP-HPLC (Table 2, Method b) to give 5-(1-((cis-4-aminocyclohexyl)methyl)-1H-pyrazolo[3,4-d]pyrimidin-6-ylamino)-2-methylbenzenesulfonamide (0.435 g. 95%) as a white solid. LC/MS (Table 2, Method a) $R_t$=1.39 min; MS m/z: 414 (M+H)$^+$.

TABLE C.1

Examples prepared using General Procedure C

| Boc protected amine | Product | Ex. # | $R_t$ min (method) | m/z ESI+ (M + H)$^+$ |
|---|---|---|---|---|
| tert-butyl ((1R,4R)-4-((6-(4-methyl-3-sulfamoylphenylamino)-1H-pyrazolo[3,4-d]pyrimidin-1-yl)methyl)cyclohexyl)methylcarbamate (prepared using B from Example #A.1.1 and 5-amino-2-methylbenzenesulfonamide [Waterstone]) | | C.1.2 | 1.48 (a) | 430 |
| tert-butyl ((1R,4R)-4-((6-(4-(4-methylpiperazin-1-yl)phenylamino)-1H-pyrazolo[3,4-d]pyrimidin-1-yl)methyl)cyclohexyl)methylcarbamate (Example #B.1.2) | | C.1.3 | 1.35 (a) | 435 |
| tert-butyl (1R,4R)-4-((6-(4-(4-methylpiperazin-1-yl)phenylamino)-1H-pyrazolo[3,4-d]pyrimidin-1-yl)methyl)cyclohexylcarbamate (Example #B.1.5) | | C.1.4 | 1.36 (a) | 421 |
| tert-butyl 4-(6-(4-methyl-3-sulfamoylphenylamino)-1H-pyrazolo[3,4-d]pyrimidin-1-yl)piperidine-1-carboxylate (Example #B.1.6) | | C.1.5 | 1.39 (a) | 388 |

TABLE C.1-continued

Examples prepared using General Procedure C

| Boc protected amine | Product | Ex. # | R$_t$ min (method) | m/z ESI+ (M + H)+ |
|---|---|---|---|---|
| tert-butyl 4-(6-(4-(4-methylpiperazin-1-yl)phenylamino)-1H-pyrazolo[3,4-d]pyrimidin-1-yl)piperidine-1-carboxylate (Example #B.1.7) | | C.1.6 | 1.31 (a) | 393 |
| tert-butyl (1S,4S)-4-(6-(4-methyl-3-sulfamoylphenylamino)-1H-pyrazolo[3,4-d]pyrimidin-1-yl)cyclohexylcarbamate (Example #B.1.8) | | C.1.7 | 1.43 (a) | 402 |
| tert-butyl (1S,4S)-4-((6-amino-1H-pyrazolo[3,4-d]pyrimidin-1-yl)methyl)cyclohexylcarbamate (Example #A.1.2) | | C.1.8 | 0.95 (a) | 247 |
| [tert-butyl (1r,4r)-4-((6-chloro-1H-pyrazolo[3,4-d]pyrimidin-1-yl)methyl)cyclohexylcarbamate | | C.1.9 | | |

TABLE C.2

Examples prepared using General Procedure C

| Boc protected amine | Product | Ex. # | NMR | m/z ESI+ (M + H)+ |
|---|---|---|---|---|
| tert-butyl ((1R,4R)-4-((6-(1-methyl-1H-pyrazol-4-ylamino)-1H-pyrazolo[3,4-d]pyrimidin-1-yl)methyl)cyclohexyl)methylcarbamate (Example #B.2.1) | | C.2.1 | 1H NMR (300 MHz, DMSO-D6) δ ppm 1.03-1.37 (m, 4 H) 1.65 (d, J = 11.5 Hz, 2 H) 1.79-2.00 (m, 3 H) 2.95 (br s, 1 H) 3.84 (s, 3 H) 4.18 (d, J = 6.4 Hz, 2 H) 7.49-7.82 (m, 3 H) 7.97 (s, 1 H) 8.03 (s, 1 H) 8.90 (s, 1 H) 9.80 (br s, 1 H) | 327 |
| tert-butyl ((1R,4R)-4-((6-(1-(2-hydroxyethyl)-1H-pyrazol-4-ylamino)-1H-pyrazolo[3,4-d]pyrimidin-1-yl)methyl)cyclohexyl)methylcarbamate (Example #B.2.2) | | C.2.2 | 1H NMR (300 MHz, DMSO-D6) δ ppm 0.79-0.98 (m, 1 H) 0.99-1.44 (m, 5 H) 1.66 (d, J = 10.5 Hz, 2 H) 1.77-2.02 (m, 2 H) 2.94 (s, 1 H) 3.74 (t, J = 5.3 Hz, 2 H) 4.03-4.32 (m, 3 H) 7.49-7.84 (m, 3 H) 8.02 (s, 1 H) 8.08 (s, 1 H) 8.90 (s, 1 H) 9.80 (br s, 1 H) | 357 |
| tert-butyl (1r,4r)-4-((6-(3-(2-hydroxyethylsulfonyl)phenylamino)-1H-pyrazolo[3,4-d]pyrimidin-1-yl)methyl)cyclohexylcarbamate | | C.2.3 | 1H NMR (300 MHz, DMSO) δ 10.43-10.37 (m, 1H), 9.09 (d, J = 7.5 Hz, 1H), 9.08-9.04 (m, 1H), 8.15 (s, 1H), 7.92-7.34 (m, 3H), 4.68 (t, J = 5.4 Hz, 1H), 4.26-4.11 (m, 2H), 3.92 (t, J = 5.5 Hz, 1H), 3.77-3.58 (m, 1H), 3.46 (t, J = 6.5 Hz, 2H), 3.01-2.87 (m, 1H), 1.96-1.86 (m, 3H), 1.70-1.60 (m, 2H), 1.31-1.17 (m, 5H), 0.96-0.83 (m, 1H) | 431 |

TABLE C.2-continued

Examples prepared using General Procedure C

| Boc protected amine | Product | Ex. # | NMR | m/z ESI+ (M + H)+ |
|---|---|---|---|---|
| tert-butyl (1r,4r)-4-((6-(3-(N-(pyridin-3-ylmethyl)sulfamoyl)phenylamino)-1H-pyrazolo[3,4-d]pyrimidin-1-yl)methyl)cyclohexylcarbamate | | C.2.4 | $^1$H NMR (300 MHz, DMSO) δ 10.34 (s, 1H), 9.73 (s, 1H), 9.05 (s, 1H), 8.15 (s, 1H), 8.05-7.98 (m, 2H), 7.72-7.60 (m, 4H), 7.49-7.20 (m, 1H), 7.03-6.96 (m, 2H), 6.83-6.76 (m, 2H), 4.24-4.17 (m, 2H), 2.98-2.84 (m, 1H), 1.96-1.85 (m, 1H), 1.71-1.60 (m, 3H), 1.33-1.02 (m, 4H). | 493 |
| tert-butyl (1r,4r)-4-((6-(4-(N-(4-methoxyphenyl)sulfamoyl)phenylamino)-1H-pyrazolo[3,4-d]pyrimidin-1-yl)methyl)cyclohexylcarbamate (Example #C.1.9) | | C.2.5 | $^1$H NMR (300 MHz, DMSO) δ 10.34 (s, 1H), 9.73 (s, 1H), 9.05 (s, 1H), 8.15 (s, 1H), 8.05-7.98 (m, 2H), 7.72-7.60 (m, 4H), 7.49-7.20 (m, 1H), 7.03-6.96 (m, 2H), 6.83-6.76 (m, 2H), 4.24-4.17 (m, 2H), 3.63 (d, J = 19.6 Hz, 2H), 2.98-2.84 (m, 1H), 1.96-1.85 (m, 3H), 1.71-1.60 (m, 2H), 1.33-1.02 (m, 4H). | 508 |

General Procedure D: Formation of an Amide from an Activated Acid and an Amine

A flask is charged with an amine (preferably 1 equiv), a basic organic catalyst (such as DMAP, 0.01-0.1 equiv, preferably 0.05 equiv) and an organic base (such as TEA, preferably in over 100 fold excess) in an organic solvent (such as THF or DCM, preferably THF). An acid chloride (1-5 equiv, preferably 1.1 equiv) is added, and the resulting reaction mixture is allowed to stir at about 0-50° C. (preferably about ambient temperature) for about 0.5-24 h (preferably about 2 h). Additional acid chloride (0.2-2.0 equiv, preferably 0.2 equiv) is added, as needed, until the starting amine is consumed, as monitored by TLC, LC/MS, or HPLC. The reaction mixture is concentrated under reduced pressure and the crude product is purified by crystallization or trituration from an appropriate solvent or solvents, or by chromatography to give the target compound.

Illustration of General Procedure D

Example #D.1.1

N-(cis-4-((6-(4-Methyl-3-sulfamoylphenylamino)-1H-pyrazolo[3,4-d]pyrimidin-1-ylmethyl)cyclohexyl)acetamide

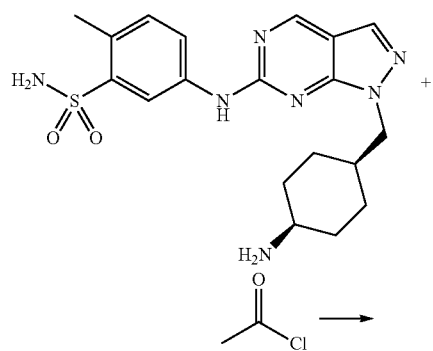

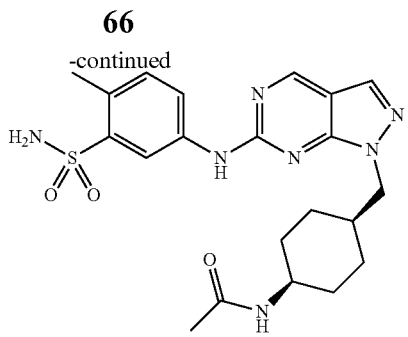

Acetyl chloride (0.027 mL, 0.38 mmol) was added to a 10 mL vial charged with 5-(1-((cis-4-aminocyclohexyl)methyl)-1H-pyrazolo[3,4-d]pyrimidin-6-ylamino)-2-methylbenzenesulfonamide (0.15 g, 0.36 mmol, Example #C.1.1) and TEA (1 mL) in THF (4 mL). The reaction mixture was stirred at ambient temperature for about 2 h, then concentrated under reduced pressure. The crude product was purified by RP-HPLC (Table 2, Method b) to give N-(cis-4-((6-(4-methyl-3-sulfamoylphenylamino)-1H-pyrazolo[3,4-d]pyrimidin-1-yl)methyl)cyclohexyl)acetamide (0.021 g, 13%) as a white solid. LC/MS (Table 2, Method a) $R_t$=1.71 min; MS m/z: 458 (M+H)$^+$.

TABLE D.1

Examples prepared from 5-(1-((cis-4-aminocyclohexyl)methyl)-1H-pyrazolo[3,4-d]pyrimidin-6-ylamino)-2-methylbenzenesulfonamide (Example #C.1.1) using General Procedure D

| Acid Chloride | Product | Ex. # | $R_t$ min (method) | m/z ESI+ (M + H)$^+$ |
|---|---|---|---|---|
| 3,3-Dimethyl butanoyl chloride | | D.1.2 | 2.42 (a) | 612 |
| 3,3-Dimethyl butanoyl chloride | | D.1.3 | 2.05 (a) | 514 |

Example #1

N-(2-methoxyphenyl)-1-(pyridin-2-yl)-1H-pyrazolo[3,4-d]pyrimidin-6-amine

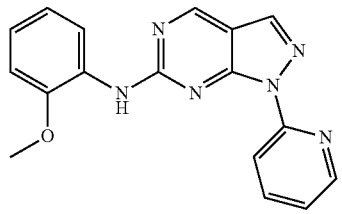 [SMILES: COc1ccccc1Nc1ncc2cnn(-c3ccccn3)c2n1]

N-(2-methoxyphenyl)-1H-pyrazolo[3,4-d]pyrimidin-6-amine, hydrochloride (150 mg, 0.540 mmol) was added to a microwave vial and charged with DMF (3 mL). Added cesium carbonate (352 mg, 1.080 mmol) and stirred for 5 min followed by addition of 2-iodopyridine (0.076 mL, 0.702 mmol), trans-N,N-dimethylcyclohexane-1,2-diamine (0.020 mL, 0.124 mmol) and copper(I) iodide (7.20 mg, 0.038 mmol). The solution was bubbled with $N_2$ for 5 min then sealed and heated at about 110° C. under $N_2$ for about 16 h. The solution was diluted with water and extracted with EtOAc/THF several times, dried with $MgSO_4$, filtered, concentrated and purified by reverse phase HPLC (Table 2, Method b) to give N-(2-methoxyphenyl)-1-(pyridin-2-yl)-1H-pyrazolo[3,4-d]pyrimidin-6-amine trifluoroacetate (10 mg, 4.5%) as a pale orange solid LC/MS (Table 2, Method a) $R_t$=1.47 min; MS m/z: 319 (M+1).

Example #2

2-(6-(2-Methoxyphenylamino)-1H-pyrazolo[3,4-d]pyrimidin-1-yl)-N-methylbenzenesulfonamide

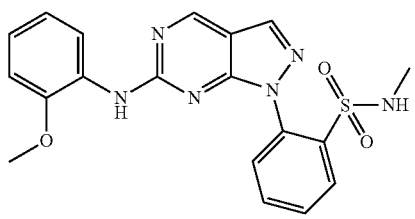 [SMILES: CNS(=O)(=O)c1ccccc1-n1ncc2cnc(Nc3ccccc3OC)nc21]

N-(2-methoxyphenyl)-1H-pyrazolo[3,4-d]pyrimidin-6-amine (0.115 g, 0.477 mmol), 2-(N-methylsulfamoyl)phenylboronic acid (0.205 g, 0.953 mmol), copper(II) acetate (0.130 g, 0.715 mmol) and activated 3 Å molecular sieves (0.296 g, 1.421 mmol) were suspended in DMF (3 mL) followed by addition of pyridine (0.077 mL, 0.953 mmol) and stirred at ambient temperature with a drying tube affixed open to air. The solution was stirred at ambient temperature for about 16 h then heated in an oil bath overnight at about 65° C. The solution was filtered through a Celite® pad washing with EtOAc/THF, then concentrated and purified by reverse phase HPLC (Table 2, Method b), to give 2-(6-(2-methoxyphenylamino)-1H-pyrazolo[3,4-d]pyrimidin-1-yl)-N-methylbenzenesulfonamide trifluoroacetate (12 mg, 5%) as a light yellow solid. LC/MS (Table 2, Method a) $R_t$=1.63 min; MS m/z: ESI+ (M+1)=411.

What is claimed:

1. A compound of Formula (I)

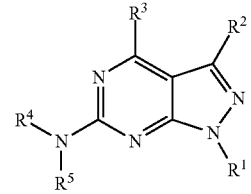

Formula (I)

a pharmaceutically acceptable salt or stereoisomer thereof wherein
  $R^1$ is —W—X—Y wherein W is directly attached to the nitrogen of the pyrazolyl ring;
  W is phenylene, optionally substituted $(C_1-C_6)$alkylene, optionally substituted bridged $(C_2-C_{10})$heterocyclylene, $(C_3-C_6)$cycloalkylene, optionally substituted heterocyclylene or optionally substituted heteroarylene;
  X is a bond, phenylene, optionally substituted $(C_3-C_6)$cycloalkylene, optionally substituted piperidinyl or optionally substituted heteroarylene;
  Y is deuterium, —C(O)$R^a$, —S(O)$_2$N($R^a$)$_2$, —N($R^a$)S(O)$_2$, —O$R^a$, —N($R^a$)S(O)$_2$$R^a$, —C(O)N($R^a$)$_2$, —N($R^a$)C(O)$R^a$, —N($R^a$)$_2$, S(O)$_2$$R^a$, —CH$_3$, —CH$_2$NH$_2$, -optionally substituted $(C_1-C_6)$alkylene, —N($R^a$)C(O)O—$R^a$, or optionally substituted $(C_1$-$C_6)$alkyl, provided that when W and X are both bonds then Y is not oxo, —N($R^a$)S(O)$_2$$R^a$, —N($R^a$)C(O)$R^a$ or —N($R^a$)$_2$; or
  Y is A-D wherein A is connected to X wherein
    A is a bond, C(O), C(O)$R^b$, $R^b$C(O), S(O)$_2$, optionally substituted $(C_1-C_6)$alkylene, N($R^a$)S(O)$_2$$R^b$, $R^b$S(O)$_2$N($R^a$), N($R^a$)C(O), C(O)N($R^a$), N($R^a$)S(O)$_2$, S(O)$_2$N($R^a$), O, O$R^b$, $R^b$O, N($R^a$)$R^b$, $R^b$N($R^a$), $R^b$N($R^a$)C(O), C(O)N($R^a$)$R^b$, $R^b$N($R^a$)S(O)$_2$, S(O)$_2$N($R^a$)$R^b$, N($R^a$)C(O)$R^b$, $R^b$C(O)N($R^a$), $R^b$N($R^a$), S(O)$_2$$R^b$, $R^b$S(O)$_2$, and N($R^a$); and
    D is —CN, —C(O)N($R^a$)$_2$ or N($R^a$)$_2$; or
    D is —O-optionally substituted $(C_1-C_6)$alkyl, optionally substituted aryl, optionally substituted $(C_3$-$C_{10})$cycloalkyl, optionally substituted heterocyclyl or optionally substituted heteroaryl;
      wherein D may be optionally substituted by one or more CN, halogen, —OH, —C(O)$R^a$, —$R^a$, —C(O)N($R^a$)$_2$, —O—$R^a$, —N($R^a$)S(O)$_2$$R^a$, —S—$R^a$, —S(O)—$R^a$, —S(O)$_2$—$R^a$ or —S(O)$_2$N($R^a$)$_2$;
  provided that $R^1$ is not biphenyl, optionally substituted indanyl, optionally substituted indenyl, optionally substituted indolyl or optionally substituted tetrahydrofuranyl; or
  $R^1$ is

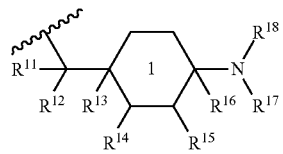

wherein $R^{11}$, $R^{12}$, $R^{13}$, $R^{14}$, $R^{15}$ and $R^{16}$ are independently H, CN, OH, optionally substituted $(C_1-C_6)$alkyl, —O-optionally substituted $(C_1-C_6)$alkyl or optionally substituted $(C_3-C_{10})$cycloalkyl;

$R^{17}$ and $R^{18}$ are independently H, —S(O)$_2$-optionally substituted (C$_3$-C$_{10}$)cycloalkyl, —S(O)$_2$-optionally substituted aryl, —S(O)$_2$-optionally substituted (C$_1$-C$_6$)alkyl, —S(O)$_2$, —S(O)$_2$-optionally substituted heterocyclyl, —S(O)$_2$-optionally substituted heteroaryl, —C(O)-optionally substituted (C$_3$-C$_{10}$)cycloalkyl, —C(O)-optionally substituted aryl, —C(O)-optionally substituted (C$_1$-C$_6$)alkyl, —C(O)-optionally substituted heterocyclyl- or —C(O)-optionally substituted heteroaryl; or $R^{17}$ and $R^{18}$ form a heterocyclic ring together with the nitrogen to which they are attached;

or $R^2$ is H;
$R^3$ is H;
$R^4$ is H;
$R^5$ is -G-J wherein G is connected to the nitrogen atom and wherein
  G is a bond, pyrazole or phenylene;
    wherein the phenylene is optionally substituted with CH$_3$; and
  J is H, optionally substituted (C$_1$-C$_3$)alkyl, —OR$^a$, —C(O)R$^a$, —S(O)$_2$—R$^b$, —S(O)$_2$—N(R$^a$)$_2$, optionally substituted thiomorpholinyl or optionally substituted piperazinyl;
    wherein the piperazinyl is optionally substituted with CH$_3$ and provided that J is not triazolyl; or $R^4$ and $R^5$ fuse to form a (C$_2$-C$_4$)heterocyclic ring which can be optionally substituted;

$R^a$ is independently H, deuterium, optionally substituted (C$_1$-C$_6$)alkyl, optionally substituted (C$_3$-C$_{10}$)cycloalkyl, optionally substituted aryl, or optionally substituted heteroaryl; and $R^b$ is independently optionally substituted (C$_1$-C$_6$)alkyl, optionally substituted (C$_3$-C$_{10}$)cycloalkyl, optionally substituted aryl, optionally substituted heteroaryl or optionally substituted heterocyclyl;

and provided that the compound is not
  1-isopropyl-4-methyl-N-(5-(piperazin-1-yl)pyridin-2-yl)-1H-pyrazolo[3,4-d]pyrimidin-6-amine;
  tert-butyl 4-(6-(4-(4-methylpiperazin-1-yl)phenylamino)-1H-pyrazolo[3,4-d]pyrimidine-1-yl)cyclohexyl carbamate;
  1-cyclopentyl-N-(4-(4-methylpiperazin-1-yl)phenyl)-1H-pyrazolo[3,4-d]pyrimdin-6-amine;
  1-cyclohexyl-N-(4-(4-methylpiperazin-1-yl)phenyl)-1H-pyrazolo[3,4-d]pyrimidine-6-amine;
  1-cyclohexyl-N-(4-(piperazin-1-yl)phenyl)-1H-pyrazolo[3,4-d]pyrimidin-6-amine; or
  tert-butyl 4-((1-cyclohexyl-1H-pyrazolo[3,4-d]pyrimidin-6-yl)amino)benzoate.

2. The compound according to claim 1 wherein $R^4$ is H.

3. The compound of claim 2 wherein
$R^1$ is —W—X—Y wherein W is directly attached to the nitrogen of the pyrazolyl ring;
W is optionally substituted (C$_1$-C$_6$)alkylene, phenylene, (C$_3$-C$_6$)cycloalkylene, optionally substituted heterocyclylene or optionally substituted heteroarylene;
X is a bond, phenylene, optionally substituted (C$_3$-C$_6$)cycloalkylene, optionally substituted piperidinyl or optionally substituted pyridinyl;
Y is —C(O)R$^a$, —S(O)$_2$N(R$^a$)$_2$, —N(R$^a$)S(O)$_2$, —OR$^a$, N(R$^a$)S(O)$_2$R$^a$, —C(O)N(R$^a$)$_2$, —N(R$^a$)C(O)R$^a$, N(R$^a$)$_2$, S(O)$_2$R$^a$, CH$_3$ or CH$_2$NH$_2$, provided that when W and X are both bonds that Y is not oxo, —N(R$^a$)S(O)$_2$, —N(R$^a$)S(O)$_2$R$^a$, N(R$^a$)C(O)R$^a$ or N(R$^a$)$_2$; or Y is A-D wherein A is connected to X wherein
A is a bond, C(O), C(O)R$^b$, R$^b$C(O), S(O)$_2$, optionally substituted (C$_1$-C$_6$)alkylene, N(R$^a$)S(O)$_2$R$^b$, N(R$^a$)C(O), C(O)N(R$^a$), N(R$^a$)S(O)$_2$, S(O)$_2$N(R$^a$), O, OR$^b$, R$^b$O, N(R$^a$)R$^b$, R$^b$N(R$^a$), R$^b$N(R$^a$)C(O), C(O)N(R$^a$)R$^b$, R$^b$N(R$^a$)S(O)$_2$, N(R$^a$)C(O)R$^b$, R$^b$C(O)N(R$^a$), R$^b$N(R$^a$), R$^b$N(R$^a$)S(O)$_2$, S(O)$_2$R$^b$, R$^b$S(O)$_2$, or N(R$^a$); and D is —CN, —C(O)N(R$^a$)$_2$ or N(R$^a$)$_2$; or D is —O-optionally substituted (C$_1$-C$_6$)alkyl, optionally substituted aryl, optionally substituted (C$_3$-C$_{10}$)cycloalkyl, optionally substituted heterocyclyl or optionally substituted heteroaryl;
  wherein D may be optionally substituted by one or more CN, halogen, OH, —C(O)— (C$_1$-C$_6$)alkyl, —C(O)N(R$^a$)$_2$, —O—(C$_1$-C$_6$)alkyl, —N(R$^a$)S(O)$_2$R$^a$, —S—(C$_1$-C$_6$)alkyl, —S(O)—(C$_1$-C$_6$)alkyl, —S(O)$_2$—(C$_1$-C$_6$)alkyl or —S(O)$_2$N(R$^a$)$_2$.

4. The compound of claim 3 wherein
Y is A-D wherein A is connected to X wherein
A is a bond, C(O), C(O)R$^b$, R$^b$C(O), S(O)$_2$, optionally substituted (C$_1$-C$_6$)alkylene, N(R$^a$)S(O)$_2$R$^b$, N(R$^a$)C(O), C(O)N(R$^a$), N(R$^a$)S(O)$_2$, S(O)$_2$N(R$^a$), O, OR$^b$, R$^b$O, N(R$^a$)R$^b$, R$^b$N(R$^a$), R$^b$N(R$^a$)C(O), C(O)N(R$^a$)R$^b$, R$^b$N(R$^a$)S(O)$_2$, N(R$^a$)C(O)R$^b$, R$^b$C(O)N(R$^a$), R$^b$N(R$^a$), R$^b$N(R$^a$)S(O)$_2$, S(O)$_2$R$^b$, R$^b$S(O)$_2$, or N(R$^a$); and D is —CN, —C(O)N(R$^a$)$_2$ or —N(R$^a$)$_2$; or D is, —O-optionally substituted (C$_1$-C$_6$)alkyl, optionally substituted aryl, optionally substituted (C$_3$-C$_{10}$) cycloalkyl, optionally substituted heterocyclyl or optionally substituted heteroaryl;
  wherein D may be optionally substituted by one or more —CN, halogen, —OH, —C(O)— (C$_1$-C$_6$) alkyl, —C(O)N(R$^a$)$_2$, —O—(C$_1$-C$_6$)alkyl, —N(R$^a$)S(O)$_2$R$^a$, —S—(C$_1$-C$_6$)alkyl, —S(O)—(C$_1$-C$_6$)alkyl, —S(O)$_2$—(C$_1$-C$_6$)alkyl or —S(O)$_2$N(R$^a$)$_2$.

5. The compound of claim 3 wherein
Y is —S(O)$_2$N(R$^a$)$_2$, —N(R$^a$)S(O)$_2$, —OR$^a$, —C(O)N(R$^a$)$_2$, —N(R$^a$)C(O)R$^a$, —N(R$^a$)$_2$, —CH$_3$ or —CH$_2$NH$_2$; or Y is A-D wherein
A is a bond, C(O), S(O)$_2$, optionally substituted (C$_1$-C$_6$) alkylene, N(R$^a$)S(O)$_2$R$^b$, N(R$^a$)C(O), C(O)N(R$^a$), N(R$^a$)S(O)$_2$, S(O)$_2$N(R$^a$), O, OR$^b$, R$^b$N(R$^a$), R$^b$N(R$^a$)C(O), C(O)N(R$^a$)R$^b$, R$^b$N(R$^a$)S(O)$_2$, N(R$^a$)C(O)R$^b$, or R$^b$C(O)N(R$^a$), and D is CN, —C(O)N(R$^a$)$_2$, N(R$^a$)$_2$, or —O-optionally substituted (C$_1$-C$_6$)alkyl; or D is optionally substituted aryl, optionally substituted (C$_3$-C$_{10}$)cycloalkyl, optionally substituted heterocyclyl or optionally substituted heteroaryl;
  wherein D may be optionally substituted by one or more —CN, halogen, —OH, —C(O)— (C$_1$-C$_6$) alkyl, —C(O)N(R$^a$)$_2$, —O—(C$_1$-C$_6$)alkyl, —N(R$^a$)S(O)$_2$R$^a$, —S—(C$_1$-C$_6$)alkyl, —S(O)— (C$_1$-C$_6$)alkyl, —S(O)$_2$—(C$_1$-C$_6$)alkyl or —S(O)$_2$N(R$^a$)$_2$.

6. The compound of claim 5 wherein
W is optionally substituted (C$_1$-C$_6$)alkylene;
X is a bond, phenylene, optionally substituted (C$_3$-C$_6$) cycloalkylene, or optionally substituted piperidinyl;

Y is —S(O)₂N(Rᵃ)₂, —N(Rᵃ)S(O)₂, —ORᵃ, —C(O)N(Rᵃ)₂, —N(Rᵃ)C(O)Rᵃ, —N(Rᵃ)₂, or optionally substituted (C₁-C₆)alkyl; or
Y is A-D wherein A is connected to X wherein
A is a bond, C(O), N(Rᵃ)C(O), or RᵇN(Rᵃ)C(O); and
D is —CN, —C(O)N(Rᵃ)₂, —N(Rᵃ)₂, or —O-optionally substituted (C₁-C₆)alkyl.

7. The compound of claim 6 wherein
R⁴ is H or optionally substituted (C₁-C₄)alkyl;
R⁵ is -G-J wherein G is connected to the nitrogen atom and wherein
G is a bond, pyrazole or phenylene;
wherein the phenylene is optionally substituted with CH₃; and
J is H, optionally substituted (C₁-C₃)alkyl, —OH, —OCH₃, —C(O)Ra, —C(O)N(Rᵃ)₂, —SRᵃ—, —S(O)₂-optionally substituted (C₁-C₃)alkyl, —S(O)₂—N(Rᵃ)₂, -optionally substituted phenyl, optionally substituted thiomorpholinyl or optionally substituted piperazinyl;
wherein Rᵃ is independently H or optionally substituted (C₁-C₆)alkyl.

8. The compound of claim 2 wherein

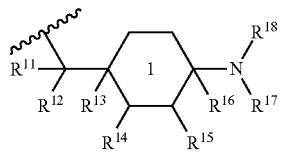

R¹ is
wherein R¹¹, R¹², R¹³, R¹⁴, R¹⁵ and R¹⁶ are independently H, —CN, —OH, optionally substituted (C₁-C₆)alkyl, —O-optionally substituted (C₁-C₆)alkyl or optionally substituted (C₃-C₁₀)cycloalkyl; or
R¹³ and R¹⁶ together form an optionally substituted carbocyclic ring or an optionally substituted heterocyclic ring; or
R¹¹ and R¹² together form an optionally substituted carbocyclic ring, an optionally substituted heterocyclic ring or an optionally substituted spirocyclic ring; or
R¹¹ and R¹³ together form an optionally substituted carbocyclic ring or optionally substituted heterocyclic ring; or
R¹⁶ and R¹⁷ together form an optionally substituted carbocyclic ring or optionally substituted heterocyclic ring; or
R¹⁵ and R¹⁷ together with the nitrogen to which R¹⁷ is attached form heterocyclic ring fused to Ring 1; or
R¹⁷ and R¹⁸ are independently H, —S(O)₂-optionally substituted (C₃-C₁₀)cycloalkyl, —S(O)₂-optionally substituted aryl, —S(O)₂-optionally substituted (C₁-C₆)alkyl, —S(O)₂, —S(O)₂-optionally substituted heterocyclyl, —S(O)₂-optionally substituted heteroaryl, —C(O)-optionally substituted (C₃-C₁₀)cycloalkyl, —C(O)-optionally substituted aryl, —C(O)-optionally substituted (C₁-C₆)alkyl, —C(O)-optionally substituted heterocyclyl- or —C(O)-optionally substituted heteroaryl; or
R¹⁷ and R¹⁸ form a heterocyclic ring together with the nitrogen to which they are attached.

9. The compound of claim 8 wherein R¹¹, R¹², R¹³, R¹⁴, R¹⁵ and R¹⁶ are independently H, CN, OH, optionally substituted (C₁-C₆)alkyl, —O-optionally substituted (C₁-C₆)alkyl or optionally substituted (C₃-C₁₀)cycloalkyl.

10. The compound of claim 8 wherein R¹³ and R¹⁶ together form an optionally substituted carbocyclic ring or an optionally substituted heterocyclic ring.

11. The compound of claim 8 wherein R¹¹ and R¹² together form an optionally substituted carbocyclic ring, an optionally substituted heterocyclic ring or an optionally substituted spirocyclic ring.

12. The compound of claim 8 wherein R¹⁶ and R¹⁷ together form an optionally substituted carbocyclic ring or optionally substituted heterocyclic ring.

13. The compound of claim 8 wherein R¹⁵ and R¹⁷ together with the nitrogen to which R¹⁷ is attached form heterocyclic ring fused to Ring 1.

14. The compound of claim 8 wherein R¹⁷ and R¹⁸ are independently H, —S(O)₂-optionally substituted (C₃-C₁₀)cycloalkyl, —S(O)₂-optionally substituted aryl, —S(O)₂-optionally substituted (C₁-C₆)alkyl, —S(O)₂, —S(O)₂-optionally substituted heterocyclyl, —S(O)₂-optionally substituted heteroaryl, —C(O)-optionally substituted (C₃-C₁₀)cycloalkyl, —C(O)-optionally substituted aryl, —C(O)-optionally substituted (C₁-C₆)alkyl, —C(O)-optionally substituted heterocyclyl- or —C(O)-optionally substituted heteroaryl; or
R¹⁷ and R¹⁸ form a heterocyclic ring together with the nitrogen to which they are attached.

15. The compound of claim 8 wherein R⁵ is -G-J wherein G is connected to the nitrogen atom and wherein
G is a bond, optionally substituted (C₃-C₁₀)cycloalkylene, pyrazole or phenylene optionally substituted with CH₃; and
J is H, optionally substituted (C₁-C₆)alkyl, —ORᵃ, —C(O)Rᵃ, —SRᵃ—, —S(O)₂—Rᵃ, —S(O)₂—N(Rᵃ)₂, —S(O)₂—NH—C(O)—Rᵃ, optionally substituted heteroaryl, or optionally substituted morpholinyl, optionally substituted thiomorpholinyl or optionally substituted piperazinyl;
wherein Rᵃ is independently H, deuterium, optionally substituted (C₁-C₆)alkyl, optionally substituted (C₃-C₁₀)cycloalkyl, or optionally substituted heteroaryl; and
Rᵇ is independently optionally substituted (C₁-C₆)alkyl, optionally substituted (C₃-C₁₀)cycloalkyl, optionally substituted aryl, optionally substituted heteroaryl or optionally substituted heterocyclyl.

16. The compound of claim 1 wherein the compound is
tert-butyl-cis-4-((6-(4-methyl-3-sulfamoylphenylamino)-1H-pyrazolo[3,4-d]pyrimidin-1-yl)methyl)cyclohexyl-carbamate;
tert-butyl((1R,4R)-4-((6-(4-(4-methylpiperazin-1-yl)phenylamino)-1H-pyrazolo[3,4-d]pyrimidin-1-yl)methyl)cyclohexyl)methylcarbamate;
3-(1-(3-(N,N-dimethylsulfamoyl)phenyl)-1H-pyrazolo[3,4-d]pyrimidin-6-ylamino)-N,N-dimethylbenzene-sulfonamide;
tert-butyl ((1R,4R)-4-((6-(3-sulfamoylphenylamino)-1H-pyrazolo[3,4-d]pyrimidin-1-yl)methyl)cyclohexyl)methylcarbamate;
tert-butyl(1R,4R)-4-((6-(4-(4-methylpiperazin-1-yl)phenylamino)-1H-pyrazolo[3,4-d]pyrimidin-1-yl)methyl)cyclohexylcarbamat;
tert-butyl 4-(6-(4-methyl-3-sulfamoylphenylamino)-1H-pyrazolo[3,4-d]pyrimidin-1-yl)piperidine-1-carboxylate;
tert-butyl 4-(6-(4-(4-methylpiperazin-1-yl)phenylamino)-1H-pyrazolo[3,4-d]pyrimidin-1-yl)piperidine-1-carboxylate;
tert-butyl 4-(6-(4-methyl-3-sulfamoylphenylamino)-1H-pyrazolo[3,4-d]pyrimidin-1-yl)cyclohexylcarbamate;

5-(1-((cis-4-aminocyclohexyl)methyl)-1H-pyrazolo[3,4-d]pyrimidin-6-ylamino)-2-methylbenzenesulfonamide;

5-(1-(((1R,4R)-4-(aminomethyl)cyclohexyl)methyl)-1H-pyrazolo[3,4-d]pyrimidin-6-ylamino)-2-methylbenzenesulfonamide;

1-(((1R,4R)-4-(aminomethyl)cyclohexyl)methyl)-N-(4-(4-methylpiperazin-1-yl)phenyl)-1H-pyrazolo[3,4-d]pyrimidin-6-amine;

1-(((1R,4R)-4-aminocyclohexyl)methyl)-N-(4-(4-methylpiperazin-1-yl)phenyl)-1H-pyrazolo[3,4-d]pyrimidin-6-amine;

N-(4-(4-methylpiperazin-1-yl)phenyl)-1-(piperidin-4-yl)-1H-pyrazolo[3,4-d]pyrimidin-6-amine;

5-(1-(4-aminocyclohexyl)-1H-pyrazolo[3,4-d]pyrimidin-6-ylamino)-2-methylbenzenesulfonamide;

1-(((1S,4S)-4-aminocyclohexyl)methyl)-1H-pyrazolo[3,4-d]pyrimidin-6-amine;

1-(((1R,4R)-4-aminocyclohexyl)methyl)-N-(1-methyl-1H-pyrazol-4-yl)-1H-pyrazolo[3,4-d]pyrimidin-6-amine;

2-(4-(1-(((1R,4R)-4-aminocyclohexyl)methyl)-1H-pyrazolo[3,4-d]pyrimidin-6-ylamino)-1H-pyrazol-1-yl)propan-1-ol;

N-(cis-4-((6-(4-Methyl-3-sulfamoylphenylamino)-1H-pyrazolo[3,4-d]pyrimidin-1-yl)methyl)cyclohexyl)acetamide;

N-(5-1-(((1S,4S)-4-(3,3-dimethylbutanamido)cyclohexyl)methyl)-1H-pyrazolo[3,4-d]pyrimidin-6-ylamino)-2-methylphenylsulfonyl)-3,3-dimethylbutanamide;

3,3-dimethyl-N-((1S,4S)-4-((6-(4-methyl-3-sulfamoylphenylamino)-1H-pyrazolo[3,4-d]pyrimidin-1-yl)methyl)cyclohexyl)butanamide;

3-((1-(cyclohexylmethyl)-1H-pyrazolo[3,4-d]pyrimidin-6-yl)methyl)benzenesulfonamide;

3-((1-(cyclohexylmethyl)-1H-pyrazolo[3,4-d]pyrimidin-6-yl)methyl)benzenesulfonamide;

N-(1-cyclohexylmethyl-1H-pyrazolo[3,4-d]pyrimidin-6-yl)-3-(1-cyclohexylmethyl-1H-pyrazolo[3,4-d]pyrimidin-6-ylmethyl)-benzenesulfonamide;

1-(cyclohexylmethyl)-N-(4-(4-methylpiperazin-1-yl)phenyl)-1H-pyrazolo[3,4-d]pyrimidin-6-amine;

tert-butyl((1R,4R)-4-((6-(4-cyclohexylphenylamino)-1H-pyrazolo[3,4-d]pyrimidin-1-yl)methyl)cyclohexyl)methylcarbamate;

1-(((1R,4R)-4-(aminomethyl)cyclohexyl)methyl)-N-(4-cyclohexylphenyl)-1H-pyrazolo[3,4-d]pyrimidin-6-amine;

4-(1-(((1R,4R)-4-aminocyclohexyl)methyl)-1H-pyrazolo[3,4-d]pyrimidin-6-ylamino)-N,N-dimethylbenzenesulfonamide;

4-(1-(((1R,4R)-4-aminocyclohexyl)methyl)-1H-pyrazolo[3,4-d]pyrimidin-6-ylamino)-N-cyclopropylbenzenesulfonamide;

3-(1-(((1R,4R)-4-aminocyclohexyl)methyl)-1H-pyrazolo[3,4-d]pyrimidin-6-ylamino)benzamide;

[1-(4-amino-cyclohexylmethyl)-1H-pyrazolo[3,4-d]pyrimidin-6-yl]-[4-(1,1-dioxo-thiomorpholin-4-yl)-phenyl]-amine;

1-(((1R,4R)-4-aminocyclohexyl)methyl)-N-(4-(methylsulfonyl)phenyl)-1H-pyrazolo[3,4-d]pyrimidin-6-amine;

2-(4-(1-(((1R,4R)-4-aminocyclohexyl)methyl)-1H-pyrazolo[3,4-d]pyrimidin-6-ylamino)phenylsulfonyl)ethanol;

4-(1-(((1R,4R)-4-aminocyclohexyl)methyl)-1H-pyrazolo[3,4-d]pyrimidin-6-ylamino)-N-(pyridin-3-ylmethyl)benzenesulfonamide;

4-(1-(((1R,4R)-4-aminocyclohexyl)methyl)-1H-pyrazolo[3,4-d]pyrimidin-6-ylamino)-N-(4-methoxyphenyl)benzenesulfonamide;

4-(1-(pyridin-3-ylmethyl)-1H-pyrazolo[3,4-d]pyrimidin-6-ylamino)benzene sulfonamide;

N-(4-(4-methylpiperazin-1-yl)phenyl)-1-(pyridin-3-ylmethyl)-1H-pyrazolo[3,4-d]pyrimidin-6-amine;

[4-(1,1-dioxo-thiomorpholin-4-yl)-phenyl]-(1-pyridin-3-ylmethyl-1H-pyrazolo[3,4-d]pyrimidin-6-yl)-amine;

N1-(3-chlorophenyl)-N4-(1-(pyridin-3-ylmethyl)-1H-pyrazolo[3,4-d]pyrimidin-6-yl)benzene-1,4-diamine;

N1-(2-methoxyphenyl)-N4-(1-(pyridin-2-yl)-1H-pyrazolo[3,4-d]pyrimidin-6-yl)benzene-1,4-diamine;

2-(6-(4-(2-methoxyphenylamino)phenylamino)-1H-pyrazolo[3,4-d]pyrimidin-1-yl)-N-methylbenzene sulfonamide;

N1-(1-(cyclohexylmethyl)-1H-pyrazolo[3,4-d]pyrimidin-6-yl)-N4-phenylbenzene-1,4-diamine;

1-cyclohexylmethyl)-N-(4-(morpholinosulfonyl)phenyl)-1H-pyrazolo[3,4-d]pyrimidin-6-amine; or N1-(1-(cyclohexylmethyl)-1H-pyrazolo[3,4-d]pyrimidin-6-yl)-N4,N4-dimethylbenzene-1,4-diamine.

17. The compound
2-methyl-5-(4-(1-phenyl-1H-pyrazolo[3,4-d]pyrimidin-6-ylamino)phenylamino)benzenesulfonamide;

2-methyl-5-(1-(piperidin-4-yl)-1H-pyrazolo[3,4-d]pyrimidin-6-ylamino)benzenesulfonamide;

N-(2-methoxyphenyl)-1-(pyridin-2-yl)-1H-pyrazolo[3,4-d]pyrimidin-6-amine.

\* \* \* \* \*

UNITED STATES PATENT AND TRADEMARK OFFICE
CERTIFICATE OF CORRECTION

PATENT NO. : 8,637,529 B2  
APPLICATION NO. : 13/157777  
DATED : January 28, 2014  
INVENTOR(S) : Kevin R. Woller et al.

Page 1 of 1

It is certified that error appears in the above-identified patent and that said Letters Patent is hereby corrected as shown below:

On the title page, at item (73) Assignee delete "AbbYie Inc."

and insert -- AbbVie, Inc. --

Signed and Sealed this
Thirteenth Day of May, 2014

Michelle K. Lee
*Deputy Director of the United States Patent and Trademark Office*